(12) United States Patent
D'Angelo et al.

(10) Patent No.: US 9,296,815 B2
(45) Date of Patent: Mar. 29, 2016

(54) ANTIBODIES WITH ENHANCED OR SUPPRESSED EFFECTOR FUNCTION

(75) Inventors: Igor D'Angelo, Port Moody (CA); Dustin Bleile, Vancouver (CA); Stacey A. L. Tom-Yew, New Westminster (CA); Eric Escobar-Cabrera, Burnaby (CA); Paula I. Lario, Vancouver (CA); Anders Ohrn, Vancouver (CA); David K. Y. Poon, Richmond (CA); Surjit B. Dixit, Richmond (CA)

(73) Assignee: Zymeworks Inc., Vancouver, British Columbia (CA)

( * ) Notice: Subject to any disclaimer, the term of this patent is extended or adjusted under 35 U.S.C. 154(b) by 504 days.

(21) Appl. No.: 13/638,362

(22) PCT Filed: Mar. 28, 2011

(86) PCT No.: PCT/CA2011/000321
§ 371 (c)(1),
(2), (4) Date: Dec. 19, 2012

(87) PCT Pub. No.: WO2011/120134
PCT Pub. Date: Oct. 6, 2011

(65) Prior Publication Data
US 2013/0089541 A1    Apr. 11, 2013

Related U.S. Application Data

(60) Provisional application No. 61/318,583, filed on Mar. 29, 2010, provisional application No. 61/436,584, filed on Jan. 26, 2011.

(51) Int. Cl.
| | |
|---|---|
| *C07K 1/00* | (2006.01) |
| *C07K 16/00* | (2006.01) |
| *C07K 16/28* | (2006.01) |
| *C07K 14/735* | (2006.01) |
| *G06F 19/16* | (2011.01) |
| *C07K 16/46* | (2006.01) |
| *A61K 38/00* | (2006.01) |

(52) U.S. Cl.
CPC ........... *C07K 16/28* (2013.01); *C07K 14/70535* (2013.01); *C07K 16/283* (2013.01); *C07K 16/2851* (2013.01); *C07K 16/2887* (2013.01); *C07K 16/464* (2013.01); *G06F 19/16* (2013.01); *C07K 2317/52* (2013.01); *C07K 2317/72* (2013.01); *C07K 2317/732* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,500,362 A | 3/1996 | Robinson et al. | |
| 5,624,821 A | 4/1997 | Winter et al. | |
| 5,677,171 A | 10/1997 | Hudziak et al. | |
| 5,736,137 A | 4/1998 | Anderson et al. | |
| 5,885,573 A | 3/1999 | Bluestone et al. | |
| 6,194,551 B1 | 2/2001 | Idusogie et al. | |
| 6,737,056 B1 * | 5/2004 | Presta | 424/133.1 |
| 7,317,091 B2 | 1/2008 | Lazar et al. | |
| 7,632,497 B2 | 12/2009 | Stavenhagen | |
| 8,937,158 B2 * | 1/2015 | Lazar et al. | 530/387.3 |
| 2003/0157108 A1 | 8/2003 | Presta | |
| 2004/0002587 A1 | 1/2004 | Watkins et al. | |
| 2004/0110226 A1 * | 6/2004 | Lazar et al. | 435/7.1 |
| 2004/0132101 A1 | 7/2004 | Lazar et al. | |
| 2006/0235208 A1 | 10/2006 | Lazar et al. | |

FOREIGN PATENT DOCUMENTS

| | | |
|---|---|---|
| CN | 1705491 A | 12/2005 |
| JP | 2006524039 A | 10/2006 |
| WO | WO 99/58572 A1 | 11/1999 |
| WO | WO 00/42072 A2 | 7/2000 |
| WO | WO 2004/029207 A2 | 4/2004 |
| WO | WO 2007/022520 A2 | 2/2007 |
| WO | 2008150494 A1 | 12/2008 |
| WO | 2010106180 A3 | 9/2010 |
| WO | PCT/EP2010/053644 A2 | 9/2010 |
| WO | WO 2011/120134 | 10/2011 |

OTHER PUBLICATIONS

Alegre, et al. A non-activating "humanized" anti-CD3 monoclonal antibody retains immunosuppressive properties in vivo. Transplantation. Jun. 15, 1994;57(11):1537-43.

Armour, et al. Differential binding to human FcγRIIa and FcγRIIb receptors by human IgG wildtype and mutant antibodies. Mol Immunol. Dec. 2003;40(9):585-93.

Armour, et al. Recombinant human IgG molecules lacking Fcgamma receptor I binding and monocyte triggering activities. Eur J Immunol. Aug. 1999;29(8):2613-24.

Capel, et al. Heterogeneity of human IgG Fc receptors. Immunomethods. Feb. 1994;4(1):25-34.

(Continued)

*Primary Examiner* — Chun Dahle
(74) *Attorney, Agent, or Firm* — Kilpatrick Townsend & Stockton LLP

(57) ABSTRACT

Rationally designed antibodies and polypeptides that comprise multiple Fc region amino acid substitutions that synergistically provide enhanced selectivity and binding affinity to a target Fc receptor are provided. The polypeptides are mutated at multiple positions to make them more effective when incorporated in antibody therapeutics than those having wild-type Fc components.

14 Claims, 4 Drawing Sheets

(56) References Cited

OTHER PUBLICATIONS

Clynes, et al. Inhibitory Fc receptors modulate in vivo cytotoxicity against tumour targets. Nat Med. Apr. 2000;6(4):443-6.
CN 201180026665.4 Office action dated Dec. 19, 2013.
CN 201180026665.4 Second Office Action dated Oct. 30, 2014.
Daeron. Fc receptor biology. Annu Rev Immunol. 1997, 15:203-34.
De Haas, et al. Fc gamma receptors of phagocytes. J Lab Clin Med. Oct. 1995; 126(4):330-41.
Duncan, et al. Localization of the binding site for the human high-affinity Fc receptor on IgG. Nature. 332(7)563-4 (1988).
EP 1176161857.9 European Search Report dated Oct. 21, 2013.
Hinton, et al. Engineered human IgG antibodies with longer serum half-lives in primates. J Biol Chem. Feb. 20, 2004;279(8):6213-6. Epub Dec. 29, 2003.
Hunter, et al. Inhibition of Fcγ receptor mediated phagocytosis by nonphagocytic Fcγ receptor. Blood. Mar. 1, 1998;91(5):1762-8.
Hutchins, et al. Improved biodistribution, tumor targeting, and reduced immunogenicity in mice with a gamma 4 variant of Campath-1H. Proc Natl Acad Sci U S A. Dec. 19, 1995;92(26):11980-4.
Idusogie, et al. Engineered antibodies with increased activity to recruit complement. J Immunol. Feb. 15, 2001;166(4):2571-5.
Idusogie, et al. Mapping of the C1q binding site on rituxan, a chimeric antibody with a human IgG1 Fc. J Immunol. Apr. 15, 2000;164(8):4178-84.
Jefferis, et al. Interaction sites on human IgG-Fc for FcgammaR: current models. Immunol Lett. 82(1-2):57-65 (2002).
Jefferis, et al. Modulation of Fc(gamma)R and human complement activation by IgG3-core oligosaccharide interactions. Immunol Lett. 54(2-3):101-4 (1996).
Jefferis, et al. Recognition sites on human IgG for Fc gamma receptors: the role of glycosylation. Immunol Lett. 44(2-3):111-7 (1995).
Lazar, et al. Engineered antibody Fc variants with enhanced effector function. Proc Natl Acad Sci U S A. Mar. 14, 2006;103(11):4005-10. Epub Mar. 6, 2006.
Lund, et al. Human Fc gamma RI and Fc gamma RII interact with distinct but overlapping sites on human IgG. J Immunol. Oct. 15, 1991;147(8):2657-62.
Lund, et al. Multiple binding sites on the CH2 domain of IgG for mouse Fc gamma R11. Mol Immunol. 29(1):53-9 (1992).
Lund, et al. Multiple interactions of IgG with its core oligosaccharide can modulate recognition by complement and human Fc gamma receptor I and influence the synthesis of its oligosaccharide chains. J Immunol. 157(11):4963-9 (1996).
Lund, et al. Oligosaccharide-protein interactions in IgG can modulate recognition by Fc gamma receptors. FASEB J. Jan. 1995;9(1):115-9.
Moore, et al. Engineered Fc variant antibodies with enhanced ability to recruit complement and mediate effector functions. mAbs 2(2):181-189 (2010).

Oganesyan, et al. Structural characterization of a mutated, ADCC-enhanced human Fc fragment. Mol Immunol. Apr. 2008;45(7):1872-82.
PCT/CA2011/000321 Search Report and Written Opinion dated Jul. 15, 2011.
PCT/CA2011/000321 International Preliminary Report on Patentability dated Oct. 2, 2012.
Presta, et al. Engineering therapeutic antibodies for improved function. Biochem Soc Trans. Aug. 2002;30(4):487-90.
Presta. Antibody Engineering. Curr. Op. Struct. Biol. 1992; 2:593-596.
Ravetch, et al. Fc receptors. Annu Rev Immunol. 1991;9:457-92.
Reddy, et al. Elimination of Fc receptor-dependent effector functions of a modified IgG4 monoclonal antibody to human CD4. J Immunol. Feb. 15, 2000;164(4):1925-33.
Richards et al. "Optimization of antibody binding to FcgRIIa enhances macrophage phagocytosis of tumor cells" Molecular cancer therapeutics, American Association of Cancer Research. Aug. 1, 2008.
Shields, et al. High resolution mapping of the binding site on human IgG1 for Fc gamma RI, Fc gamma RII, Fc gamma RIII, and FcRn and design of IgG1 variants with improved binding to the Fc gamma R. J Biol Chem. Mar. 2, 2001;276(9):6591-604. Epub Nov. 28, 2000.
Shields, et al. Lack of fucose on human IgG1 N-linked oligosaccharide improves binding to human Fcgamma RIII and antibody-dependent cellular toxicity. J Biol Chem. Jul. 26, 2002;277(30):26733-40. Epub May 1, 2002.
Shinkawa, et al. The absence of fucose but not the presence of galactose or bisecting N-acetylglucosamine of human IgG1 complex-type oligosaccharides shows the critical role of enhancing antibody-dependent cellular cytotoxicity. J Biol Chem. Jan. 31, 2003;278(5):3466-73. Epub Nov. 8, 2002.
Stavenhagen, et al. Enhancing the potency of therapeutic monoclonal antibodies via Fc optimization. Adv Enzyme Regul. 48:152-64 (2008).
Stavenhagen, et al. Fc optimization of therapeutic antibodies enhances their ability to kill tumor cells in vitro and controls tumor expansion in vivo via low-affinity activating Fcgamma receptors. Cancer Res. Sep. 15, 2007;67(18):8882-90.
van Sorge et al., FcγR polymorphisms: Implications for function, disease susceptibility and immunotherapy. Tissue Antigens 61:189-202 (2003).
Veri, et al. Monoclonal antibodies capable of discriminating the human inhibitory Fcgamma-receptor IIB (CD32B) from the activating Fcgamma-receptor IIA (CD32A): biochemical, biological and functional characterization. Immunology. 121(3):392-404 (2007).
Ward, et al. The effector functions of immunoglobulins: implications for therapy. Ther Immunol. Apr. 1995;2(2):77-94.
Xu, et al. In vitro characterization of five humanized OKT3 effector function variant antibodies. Cell Immunol. 200(1):16-26 (2000).
JP2013-501570, Notice of Reasons for Rejection, mailed Jun. 2, 2015, 7 pages.
RU2012145183, Office Action, mailed Feb. 25, 2015, 8 pages.

* cited by examiner

FcγRIIIa

FcγRIIa & IIb

ANTIBODIES WITH ENHANCED OR SUPPRESSED EFFECTOR FUNCTION

CROSS-REFERENCE

This application claims priority to International Application No. PCT/CA2011/000321, filed Mar. 28, 2011, which claims priority to U.S. Provisional Application No. 61/436,584, filed Jan. 26, 2011, and U.S. Provisional Application No. 61/318,583, filed Mar. 29, 2010. The contents of the International Application and both provisional applications are incorporated in their entirety by reference herein.

FIELD OF INVENTION

The present invention relates to antibodies, fusion proteins and polypeptides. Specifically, the instant invention relates to designed antibodies and polypeptides that comprise Fc region amino acid substitutions that synergistically provide enhanced selectivity and binding affinity to a target Fc receptor.

BACKGROUND OF THE INVENTION

Antibodies are proteins which exhibit binding specificity to a specific antigen. Native antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains.

The term "variable" refers to the fact that certain portions of the variable domains differ extensively in sequence among antibodies and are responsible for the binding specificity of each particular antibody for its particular antigen. However, the variability is not evenly distributed through the variable domains of antibodies. It is concentrated in three segments called complementarity determining regions (CDRs) both in the light chain and the heavy chain variable domains. The more highly conserved portions of the variable domains are called the framework regions (FRs). The variable domains of native heavy and light chains each comprise four FRs, largely adopting a .beta.-sheet configuration, connected by three CDRs, which form loops connecting, and in some cases forming part of, the .beta.-sheet structure. The CDRs in each chain are held together in close proximity by the FRs and, with the CDRs from the other chain, contribute to the formation of the antigen binding site of antibodies (see Kabat et al., Sequences of Proteins of Immunological Interest, 5th Ed. Public Health Service, National Institutes of Health, Bethesda, Md. (1991)).

The constant domains are not involved directly in binding an antibody to an antigen, but exhibit various effector functions. Depending on the amino acid sequence of the constant region of their heavy chains, antibodies or immunoglobulins can be assigned to different classes. There are five major classes of immunoglobulins: IgA, IgD, IgE, IgG and IgM, and several of these may be further divided into subclasses (isotypes), e.g. IgG1, IgG2, IgG3, and IgG4; IgA1 and IgA2. The heavy chain constant regions that correspond to the different classes of immunoglobulins are called $\alpha$, $\delta$, $\epsilon$, $\gamma$ and $\mu$, respectively. Of the various human immunoglobulin classes, only human IgG1, IgG2, IgG3 and IgM are known to activate complement; and human IgG1 and IgG3 mediate ADCC more effectively than IgG2 and IgG4

Papain digestion of antibodies produces two identical antigen binding fragments, called Fab fragments, each with a single antigen binding site, and a residual "Fc" fragment, whose name reflects its ability to crystallize readily. The crystal structure of the human IgG Fc region has been determined (Deisenhofer, Biochemistry 20:2361-2370 (1981)). In human IgG molecules, the Fc region is generated by papain cleavage N-terminal to Cys 226. The Fc region is central to the effector functions of antibodies.

The effector functions mediated by the antibody Fc region can be divided into two categories: (1) effector functions that operate after the binding of antibody to an antigen (these functions involve the participation of the complement cascade or Fc receptor (FcR)-bearing cells); and (2) effector functions that operate independently of antigen binding (these functions confer persistence in the circulation and the ability to be transferred across cellular barriers by transcytosis). Ward and Ghetie, Therapeutic Immunology 2:77-94 (1995).

While binding of an antibody to the requisite antigen has a neutralizing effect that might prevent the binding of a foreign antigen to its endogenous target (e.g. receptor or ligand), binding alone may not remove the foreign antigen. To be efficient in removing and/or destructing foreign antigens, an antibody should be endowed with both high affinity binding to its antigen, and efficient effector functions.

Fc Receptor (FcR)

The interaction of antibodies and antibody-antigen complexes with cells of the immune system effects a variety of responses, including antibody-dependent cell-mediated cytotoxicity (ADCC) and complement dependent cytotoxicity (CDC) (reviewed in Daeron, Annu. Rev. Immunol. 15:203-234 (1997); Ward and Ghetie, Therapeutic Immunol. 2:77-94 (1995); as well as Ravetch and Kinet, Annu. Rev. Immunol. 9:457-492 (1991)).

Several antibody effector functions are mediated by Fc receptors (FcRs), which bind the Fc region of an antibody. FcRs are defined by their specificity for immunoglobulin isotypes; Fc receptors for IgG antibodies are referred to as Fc$\gamma$R, for IgE as Fc.epsilon.R, for IgA as Fc.alpha.R and so on. Three subclasses of Fc$\gamma$R have been identified in humans: Fc$\gamma$RI (CD64), Fc$\gamma$RII (CD32) and Fc$\gamma$RIII (CD16). Because each Fc$\gamma$R subclass is encoded by two or three genes, and alternative RNA spicing leads to multiple transcripts, a broad diversity in Fc$\gamma$R isoforms exists. The three genes encoding the Fc$\gamma$RI subclass (Fc$\gamma$RIA, Fc$\gamma$RIB and Fc$\gamma$RIC) are clustered in region 1q21.1 of the long arm of chromosome 1; the genes encoding Fc$\gamma$RII isoforms (Fc$\gamma$RIIA, Fc$\gamma$RIIB and Fc$\gamma$RIIC) and the two genes encoding Fc$\gamma$RII (Fc$\gamma$RIIIA and Fc$\gamma$RIIIB) are all clustered in region 1q22. These different FcR subtypes are expressed on different cell types (reviewed in Ravetch and Bollard, Annu. Rev. Immunol. 19:275-290 (2001). For example, in humans, Fc$\gamma$RIIIB is found only on neutrophils, whereas Fc$\gamma$RIIIA is found on macrophages, monocytes, natural killer (NK) cells, and a subpopulation of T-cells. Notably, Fc$\gamma$RIIIA is the only FcR present on NK cells, one of the cell types implicated in ADCC.

Fc$\gamma$RI, Fc$\gamma$RII and Fc$\gamma$RII are immunoglobulin superfamily (IgSF) receptors; Fc$\gamma$RI has three IgSF domains in its extracellular domain, while FcγRII and FcγRIII have only two IgSF domains in their extracellular domains.

Another type of Fc receptor is the neonatal Fc receptor (FcRn). FcRn is structurally similar to major histocompatibility complex (MHC) and consists of an .alpha.-chain non-covalently bound to .beta.2-microglobulin.

FcγRII (CD32), has several isoforms, IIa, IIIb1, IIb2, IIb3 and IIc, and is the most widely distributed human FcγR type, being expressed on most types of blood leukocytes, dendritic cells and platelets. FcγRII is a low affinity receptor that only binds to aggregated IgG. It is the only FcγR class to be able to bind to IgG2. The FcγRIIa is expressed on a range of cell types, including monocytes, macrophages, neutrophils, eosinophils and basophils, which it can co-activate in combination with other immunoglobulin receptors through its ITAM motifs. FcγRIIa binds IgG antibodies attached to cells and causes lysis of those cells. This process is called antibody-dependant cell mediated cytotoxicity. The FcγRIIb is also widely expressed but bears an immunoreceptor tyrosine-based inhibitory motif (ITIM) which is necessary for its inhibitory effects. FcγRIIb can suppress activation of B cells by invoking negative signaling when it is cross-linked to surface immunoglobulin via Ab-Ag complexes. The activation of macrophages and monocytes via FcγR is suppressed by co-ligation of FcγRIIb. (Armour et al. (2003) "Differential binding to human FcγRIIa and FcγRIIb receptors by human IgG wildtype and mutant antibodies," Mol. Immunol., 40:585-593). Cells transfected to express both FcγRIIa and FcγRIIb show reduced phagocytosis relative to cells bearing FcγRIIa alone and the cytotoxicity of anti-tumour Ab was enhanced in FcγRIIb-deficient mice. (Hunter et al. (1998) "Inhibition of Fcγ receptor mediated phagocytosis by nonphagocytic Fcγ receptor." Blood, 91:1762-1768; and Clynes et al. (2000) "Inhibitory Fc receptors modulate in vivo cytotoxicity against tumour targets." Nat. Med. 6:443-446). Thus, shifting relative binding affinity of FcγR from FcγRIIa to FcγRIIb, for example would suppress activation of B cells and or macrophages and monocytes and would be useful to dampen immune responses in inflammatory disorders such in various autoimmune diseases. Conversely, shifting the relative binding affinity of Fcγ from FcγRIIb to FcγRIIa would lead to an enhancement of ADCC, and would be useful to enhance tumor cell killing, for example in the treatment of cancer.

FcγRIII (CD16) has two isoforms which are able to bind to IgG1 and IgG3. The FcγRIIIa has an intermediate affinity for IgG and is expressed on macrophages, monocytes, NK cells and subsets of T cells. FcγRIIIb is a low-affinity receptor which is selectively expressed on neutrophils. FcγRIIIa, like FCγRIIa, binds to IgG antibodies attached to cells and causes the lysis of those cells by ADCC. FcγRIIIa binds clustered IgG molecules bound to cell surfaces and does not bind to monomeric IgG. Therefore, ADCC occurs only when the target cell is coated with antibody. Engagement of FcγRIIIa by antibody-coated target cells activates NK cells to synthesize and secrete cytokines such as IFN-γ, as well as discharge the contents of their granules, which mediate the cytolytic functions of this cell type.

Altering the effector activity of antibodies by shifting effector function from otherwise inhibitory immune response to inducing ADCC and vice versa is desirable for bettering treatment outcomes in a variety of diseases and conditions. Lazar et al. (2006) Proc. Natl. Acad. Sci. U.S.A., 103:4005, Stavenhagen et al. (2007) Cancer Res. 67:8882, Oganesyan et al. (2008) Mol. Immunol. 45:1872, Veri et al. (2007) Immunology, 121:392, and Shields, et al. (2001) J. Biol. Chem. 276:6591 disclose efforts in this research area.

Presta et al. (U.S. Pat. No. 6,737,056) discloses polypeptides comprising a variant Fc region. The disclosed variations are based on single position mutations. By performing alanine scans, Presta et al. discloses single position Fc region amino acid modification at positions 238, 265, 269, 270, 292, 294, 295, 298, 303, 324, 327, 329, 333, 335, 338, 373, 376, 414, 416, 419, 435, 438 or 439; these single position mutations are purported to result in reduced binding to FcγRII. Presta et al. also discloses that systematic alanine scans of the entire Fc region purportedly show that an Fc region amino acid modification at any one of amino acid positions 238, 239, 248, 249, 252, 254, 265, 268, 269, 270, 272, 278, 289, 293, 294, 295, 296, 301, 303, 322, 327, 329, 338, 340, 373, 376, 382, 388, 389, 416, 434, 435 or 437 results in reduced binding to FcγRIII. Presta et al. also discloses polypeptides with increased binding to an FcγRII comprising single position amino acid modifications at any one of amino acid positions 255, 256, 258, 267, 268, 272, 276, 280, 283, 285, 286, 290, 301, 305, 307, 309, 312, 315, 320, 322, 326, 330, 331, 337, 340, 378, 398 or 430 of the Fc region identified by alanine scans as well. Presta et al. discloses one single instance where two Fc amino acid positions are mutated at the same time (i.e., modifications S317A and K353A), however Presta et al. does not suggest that these double mutations provide any sysnergistic effect in obtaining a desired binding profile of the modified polypeptide to FcγRII. Presta et al. is completely silent on potential synergism of simultaneous modifications at more than a single amino acid position.

Lazar et al. (U.S. Pat. No. 7,317,091) discloses antibodies comprising an amino acid modification at position 332 in the Fc region purportedly resulting in altered binding to an FcγR. Lazar et al. discloses that individual substitutions in positions 234, 235, 239, 240, 243, 264, 266, 272, 274, 278, 325, 328, 330, and 332 purportedly effect the binding to an FcγR. While Lazar al. purports to disclose synergy of Fc variants when combined with engineered glycoforms, Lazar et al. is silent on potential synergism that may be provided by a selection of simultaneously modified Fc amino acid positions, regardless of additional synergism that may be provided by engineered glycoforms.

Stavenhagen (U.S. Pat. No. 7,632,497) discloses molecules having a variant Fc region, wherein the variant Fc region comprises at least one amino acid modification relative to a wild-type Fc region. These modified molecules purportedly confer an effector function to a molecule, where the parent molecule does not detectably exhibit this effector function.

Current approaches to optimize the Fc region in therapeutic monoclonal antibodies and soluble polypeptides fused to Fc regions have focused on a limited number of single amino acid changes based on alanine screens, site-directed mutagenesis etc. Other approaches in engineering Fc regions have focused on the glycosylation of the Fc region to optimize Fc region function. Still other approaches have focused on Fc modifications that purportedly confer effector function by modifying wild type molecules that lack effector function, but do not purport to increase or otherwise modify existing effector function of a wild type molecule.

There is currently no known Fc protein or polypeptide that is optimized to bind a particular FcγR of interest with very high specificity as compared to other Fcγ receptors. Although the effect of individual Fc region amino acid mutations on the binding with certain Fcγ receptors is well understood, previous studies fail to describe the effect of simultaneous changes to multiple amino acids. Additionally, the prior art does not suggest suitable replacements for substituted Fc region amino acids to obtain optimal binding to the FcγR of interest, including modification of effector function of a wild type molecule that already has detectable effector function.

Hence, there is a need in the art for polypeptides and antibodies that comprise multiple, synergistic amino acid substitutions in the Fc region such that the antibody or fusion protein is optimized for binding to the FcγR isoform of choice.

SUMMARY OF THE INVENTION

The instant compositions provide polypeptides, fusion protein and antibodies comprising Fc region that bind a target FcγR with very high specificity. These polypeptides and antibodies are designed by rational analysis of the binding of each FcγR with the Fc region and by subsequent design of multiple (three or more) amino acid substitutions that synergistically provide desired selectivity and binding affinity for the target Fc receptor. Accordingly, the polypeptides and proteins provided herein comprise multiple variations in the Fc region as compared to the wild type Fc region, said variations tailored to improving the specificity for the FcγR under consideration, and for obtaining a selected binding profile based on enthalpic and entropic factors optimized by the choice of the most favorable amino acid for each position.

One embodiment provides a polypeptide comprising a variant Fc region, wherein said variant Fc region comprises three or more amino acid modifications relative to a wild-type Fc region, and has an altered effect relative to a polypeptide comprising a wild-type Fc region; wherein at least two of the three or more modifications provide a synergistic effect compared to single position modifications at the at least two positions thereby exhibiting a selected binding profile to Fcγ receptors.

Another embodiment provides a polypeptide wherein the amino acid modifications produce amino acid interactions and dynamics that result in enhanced binding free energy to a first Fcγ receptor while diminishing binding affinity to a second Fcγ receptor compared to a polypeptide that lacks the at least three or more amino acid modifications. The first Fcγ receptor may be FcγRIIIa receptor and the second Fcγ receptor may be FcγRIIa or FcγRIIb.

Another embodiment provides a polypeptide wherein the amino acid modifications produce favorable FcγRIIIa-specific interactions and/or unfavorable interactions with FcγRIIa and/or FcγRIIb receptors.

Another embodiment provides a polypeptide wherein the amino acid modifications have minimal impact on the FcγRIIIa receptor while producing detrimental effects on binding of the polypeptide to FcγRIIa and/or FcγRIIb.

One embodiment provides a polypeptide wherein the first Fcγ receptor is FcγRIIa receptor and the second Fcγ receptor is FcγRIIIa or FcγRIIb.

One embodiment provides a polypeptide wherein the amino acid modifications produce favorable FcγRIIa-specific interactions and/or unfavorable interactions with FcγRIIIa and/or FcγRIIb receptors.

One embodiment provides a polypeptide wherein the amino acid modifications have minimal impact on the FcγRIIa receptor while producing detrimental effects on binding of the polypeptide to FcγRIIIa and/or FcγRIIb.

One embodiment provides a polypeptide wherein the Fcγ receptor with enhanced binding free energy is FcγRIIb receptor and the Fcγ receptor with diminished binding affinity is FcγRIIIa receptor or FcγRIIa receptor.

One embodiment provides a polypeptide wherein the amino acid modifications produce favorable FcγRIIb-specific interactions and/or unfavorable interactions with FcγRIIIa and/or FcγRIIa receptors.

One embodiment provides a polypeptide wherein the amino acid modifications have minimal impact on the FcγRIIb receptor while producing detrimental effects on binding of the polypeptide to FcγRIIIa and/or FcγRIIa.

One embodiment provides a polypeptide wherein the amino acid substitutions reduce or disrupt the binding affinity to the FcγRIIa receptor, the FcγRIIIa receptor and the FcγRIIb receptor when compared to the wild-type polypeptide.

One embodiment provides a polypeptide wherein binding of the polypeptide comprising a wild-type Fc region to Fcγ receptors is detectable by an in vitro assay.

In certain embodiments of the instant invention, are methods for engineering optimized Fc polypeptides and proteins. It is an object of the present disclosure to provide design strategies that may be used to guide Fc optimization. It is a further object of the present disclosure to provide computational screening methods that may be used to design Fc proteins. It is a further object of the present disclosure to provide methods for generating libraries for experimental testing. It is a further object of the present disclosure to provide experimental production and screening methods for obtaining optimized Fc proteins.

In certain embodiments are provided isolated nucleic acids encoding the Fc proteins described herein. In certain embodiments are provided vectors comprising said nucleic acids, optionally, operably linked to control sequences. In certain embodiments are provided host cells containing the vectors, and methods for producing and optionally recovering the Fc proteins.

In certain embodiments are provided antibodies and polypeptides that comprise the Fc proteins disclosed herein. Said antibodies and polypeptides may find use in a therapeutic product.

The present disclosure provides compositions comprising antibodies and polypeptides that comprise the Fc proteins described herein, and a physiologically or pharmaceutically acceptable carrier or diluent.

In certain embodiments are provided therapeutic and diagnostic uses for antibodies and polypeptides that comprise the Fc proteins disclosed herein.

Provided herein are polypeptides comprising a variant Fc region, wherein said variant Fc region comprises at least three amino acid modifications relative to a wild-type Fc region, and has an altered effect relative to a polypeptide comprising a wild-type Fc region or variant Fc region comprising only one or two amino acid modifications; and wherein at least two of the modifications provide a synergistic effect compared to single position modifications thereby exhibiting a selected binding profile to Fcγ receptors. In certain embodiments, one or both amino acid modifications are located between positions 234-330 according to the EU index. In certain embodiments, the modifications do not comprise simultaneous substitution at positions 317 and 353 according to the EU index. In some embodiments, the amino acid modifications do not comprise a substitution at position 332 according to the EU index. In certain embodiments, the polypeptides comprise the modifications L235A/S239E/D265E. In some embodiments, the polypeptides comprise the modifications A327H/E269L/K236A. In a certain embodiments, the polypeptides comprise the modifications G237F/D270Q/S239E. In some other embodiments, the polypeptides comprise the modifications A330V/I332L/K326. In one embodiment, the polypeptides comprise the modifications G236S/A327H/A330I.

In certain embodiments of the polypeptides described herein, the amino acid modifications produce amino acid interactions and dynamics that result in enhanced binding affinity and/or specificity to a first Fcγ receptor while diminishing binding affinity and/or specificity to a second Fcγ receptor compared to a polypeptide that lacks the three or more amino acid modifications. In some of these embodiments, the first Fcγ receptor is FcγRIIIa receptor and the second Fcγ receptor is FcγRIIa or FcγRIIb. In certain embodiments, the amino acid modifications produce favorable FcγRIIIa-specific interactions and/or unfavorable interactions with FcγRIIa and/or FcγRIIb receptors. In some embodiments, the amino acid modifications have minimal impact on the FcγRIIIa receptor while producing detrimental effects on binding of the polypeptide to FcγRIIa and/or FcγRIIb.

Provided herein are polypeptides comprising a variant Fc region, wherein said variant Fc region comprises at least three amino acid modifications relative to a wild-type Fc region, wherein the amino acid modifications produce amino acid interactions and dynamics that result in enhanced binding affinity and/or specificity to a FcγRIIIa receptor while diminishing binding affinity and/or specificity to FcγRIIa or FcγRIIb receptor compared to a polypeptide that lacks the two amino acid modifications. In some embodiments, the polypeptide comprises modifications S239E/D265S/I332E. In certain embodiments, the polypeptide comprises the modifications G237F/S239E/A327H. In certain other embodiments, the polypeptide comprises modifications H268D/E269L/S298A/K326A/A327H. In some embodiments, the polypeptide comprises the modifications L235A/S239E/D265E/A327H. In an embodiment, the polypeptide comprises the modifications G237F/S239E/D270N. In some embodiments, the polypeptide comprises the modifications G236E/G237F/S239E. In an embodiment, the polypeptide comprises the modifications S239E/D265SI332E and alternatively H268D. In certain embodiments, the polypeptide comprises modifications selected from the group of G237F/S239E/D265E, S239E/S298A/K326A/A327H, and G236E/D270N/A327V/I332E. In certain embodiments, the polypeptide comprises the modifications S298A/K326A/A327H wherein the polypeptide has improved binding selectivity to FcγRIIIa receptor as compared to a polypeptide lacking the S298A/K326A/A327H modifications.

In an aspect, provided herein are polypeptides comprising a variant Fc region, wherein said variant Fc region comprises at least three amino acid modifications relative to a wild-type Fc region, wherein the amino acid modifications produce amino acid interactions and dynamics that result in enhanced binding affinity and/or specificity to a FcγRIIa receptor while diminishing binding affinity and/or specificity to FcγRIIIa or FcγRIIb receptor compared to a polypeptide that lacks at least one of the amino acid modifications. In some embodiments, the polypeptide comprises modifications G237F, A327L and A330I. In certain embodiments, the amino acid modifications produce favorable FcγRIIa-specific interactions and/or unfavorable interactions with FcγRIIIa and/or FcγRIIb receptors. In certain embodiments, the amino acid modifications have minimal impact on the FcγRIIa receptor while producing detrimental effects on binding of the polypeptide to FcγRIIIa and/or FcγRIIb. In certain embodiments, the polypeptide comprises modifications G237F, S239E and H268D. In some embodiments, the polypeptide comprises modifications D265E/S267D/A330S.

In a further aspect, provided herein are polypeptides comprising a variant Fc region, wherein said variant Fc region comprises at least three amino acid modifications relative to a wild-type Fc region, wherein the amino acid modifications produce amino acid interactions and dynamics that result in enhanced binding affinity and/or specificity to a FcγRIIb receptor while diminishing binding affinity and/or specificity to FcγRIIIa or FcγRIIa receptor compared to a polypeptide that lacks at least one of the amino acid modifications. In certain embodiments, the amino acid modifications produce favorable FcγRIIb-specific interactions and/or unfavorable interactions with FcγRIIIa and/or FcγRIIa receptors. In certain embodiments, the amino acid modifications have minimal impact on the FcγRIIb receptor while producing detrimental effects on binding of the polypeptide to FcγRIIIa and/or FcγRIIa. In certain embodiments, the polypeptide comprises modifications S239D/D265S/S298A/I332E. In some other embodiments, the polypeptide comprises the modifications G237F/S298A/A330L/I332E. In some embodiments the polypeptide comprises the modifications H268D, K326A, A327H and alternatively one or both of E269L and S298A. In an embodiment, the polypeptide comprises the modifications G237F/V266L/S267D. In some embodiments, the polypeptides comprise the modifications L234F/S267G/N325L or L234F/S267E/N325L. In an embodiment, the polypeptide comprises modifications G236A/S239D/D270L/I332E.

In certain aspects described herein, the binding of the polypeptide comprising a wild-type Fc region to Fcγ receptors is detectable by an in vitro assay.

In an aspect, provided herein are polypeptides comprising a variant Fc region, wherein said variant Fc region comprises at least three amino acid modifications relative to a wild-type Fc region, wherein one of the modifications comprises the mutation S239E wherein the polypeptide has higher selectivity in binding to the FcγRIIIa receptor compared to a polypeptide that lacks the S239E mutation.

In an aspect, provided herein are polypeptides comprising a variant Fc region, wherein said variant Fc region comprises at least three amino acid modifications relative to a wild-type Fc region, wherein one of the modifications comprises the mutation S239E one of the modifications comprises the mutation S298A wherein the polypeptide has reduced binding affinity to FcγRIIa and FcγRIIb receptors compared to a polypeptide that lacks the S298A mutation.

In an aspect provided herein are polypeptides comprising a variant Fc region, wherein said variant Fc region comprises at least three amino acid modifications relative to a wild-type Fc region, said modifications selected from D270L/Y300L/A330K, G237F/S267G/N325F, G237F/V266L/S267D, L234F/S267G/N325L, L234F/S267E/N325L, G237F/S239E/A327H, G237F/A327L/A330I, S239E/A327L/A330I, S239E/S267E/H268D, G237F/S239E/D270N, G236E/G237F/S239E, S239E/D265S/I332E, G237F/S239E/D265E, G237F/S239E/H268D, H268E/D270E/S267G, H268D/K326A/A327H, D265E/S267D/A330S, L235A/S239E/D265E, A327H/E269L/K236A, G237F/D270Q/S239E, A330V/I332L/K326, and G236S/A327H/A330I.

In an aspect provided herein are polypeptides comprising a variant Fc region, wherein said variant Fc region comprises at least four amino acid modifications relative to a wild-type Fc region, said modifications selected from L235A/S239E/D265E/A327H, S239E/D265S/H268D/I332E, S239D/D265S/S298A/I332E, S239E/S298A/K326A/A327H, G237F/S298A/A330L/I332E, and G236E/D270N/A327V/I332E, G236A/S239D/D270L/I332E and H268D/E269L/S298A/K326A/A327H.

In an aspect provided herein are polypeptides comprising a variant Fc region, wherein said variant Fc region comprises at least three amino acid modifications relative to a wild-type Fc region, wherein the at least three amino acid modifications are selected from the group consisting of: L234Q, L234N, L235A, G236E, E236L, E236D, G237F, G237N, S239E, S239D, D265E, D265S, S267E, S267D, S267G, H268D, H268E, E269L, E269L, D270N, D270I, D270E, S298A, K326A, K326D, A327H, A327V, A327L, A327T, A330V, A330L, A330W, A330I, A330S, I332L, I332D, and I332E.

In an aspect provided herein are polypeptides comprising a variant Fc region, said variant Fc region comprises a combination of amino acid modifications wherein said combination is selected from the group consisting of: L235A/S239E/D265E; L235A/G237F/D265E; S239E/E269D/A327H; S239E/G237N/A327H; S239E/G237F/A327V; G237F/D270I/S239E; G237F/A327L/S239E; A327H/E269L/K326A; A330V/I332L/S239E; A327T/E269L/K326A; D270N/A327T/K326A; A330V/I332L/S239E; A330W/I332D/S239E; G236E/D265E/A327H/A330I; D270N/S298A/A327V; G236E/D265E/D270N/A327H/A330I; G236E/D270N/A327H/A330I; G236E/D270N/A327V/I332E; G236E/D270N/A327V/G237F; L234N/S239E/A330I/I332E; L234Q/S239E/A330I/I332E; L234Q/S239E/A330I/I332E/S298A; G237F/S239D/D265E/D270N/S298A; G237F/S239E/D270N/A330L/I332E; G237F/S239E/D270N/A330L/I332E/S298A; S239E/G237F/A327H; G237F/A327L/A330I; S239E/A330I/A327L; D265E/S239E/L235A/A327H; S267E/S239E/H268D; G237F/D270N/S239E; S239E/G237F/G236E; I332E/D265S/S239E/H268D; I332E/D265S/S239E; D265E/S239E/G237F; S239E/H268D/G237F; S298A/D265S/S239D/I332E; S298A/K326A/A327H/S239E; S298A/G237F/A3330L/I332E; H268E/D270E/S267G; H268D/K326A/A327H; H268D/K326A/A327H/E269L/S298A; A330S/D265E/S267D; S239E/S267E/H268D; S237F/S239E/D265E and H268E/D270/E/S267G In an aspect, provided herein are polypeptides that comprise a variant Fc region, wherein said variant Fc region comprises at least three amino acid modifications relative to a wild-type Fc region wherein when said variant Fc region comprises amino acid modification H268D, said variant does not comprise the modification S267E.

In certain embodiments of the polypeptides described herein, the Fc region of the parent polypeptide is a human IgG Fc region. In some of these embodiments, the human IgG Fc region is a human IgG1, IgG2, IgG3, or IgG4 Fc region.

In certain embodiments of the polypeptides described herein, the polypeptide is an antibody. In some embodiments, the antibody is a monoclonal antibody, a humanized antibody, or a human antibody.

In an aspect is a nucleic acid comprising: a nucleotide sequence encoding a polypeptide described herein. In certain embodiments is a vector, comprising the nucleic acid.

In an aspect is a method for producing a polypeptide or protein described herein, said method comprising: (i) culturing in a medium a host cell comprising a nucleic acid encoding said polypeptide, under conditions suitable for the expression of said polypeptide; and (ii) recovering the polypeptide from said medium.

In an aspect described herein is a therapeutic antibody that specifically binds a cancer target antigen, said therapeutic antibody comprising a variant Fc region polypeptide described herein. In certain embodiments, the therapeutic antibody is selected from the group consisting of abagovomab, adalimumab, alemtuzumab, aurograb, bapineuzumab, basiliximab, belimumab, bevacizumab, briakinumab, canakinumab, catumaxomab, certolizumab pegol, cetuximab, daclizumab, denosumab, efalizumab, galiximab, gemtuzumab ozogamicin, golimumab, ibritumomab tiuxetan, infliximab, ipilimumab, lumiliximab, mepolizumab, motavizumab, muromonab, mycograb, natalizumab, nimotuzumab, ocrelizumab, ofatumumab, omalizumab, palivizumab, panitumumab, pertuzumab, ranibizumab, reslizumab, rituximab, teplizumab, tocilizumab/atlizumab, tositumomab, trastuzumab, Proxinium™, Rencarex™, ustekinumab, zalutumumab, and any other antibodies. In certain embodiments, the target antigen is selected from the group consisting of a-chain (CD25) of IL-2R, Amyloid beta, anti-EpCAM×anti-CD3, BLyS (or BAFF), CD11a, CD20, CD22, CD23, CD3, CD4, CD52, CD80, CTLA-4, EGFR, EpCAM, F protein of RSV, G250, glycoprotein IIb/IIIa R, HER2, HER2/neu R, Hsp90, IgE antibody, IL-12/IL-23, IL-1b, IL-5, IL-6 receptor, Integrin alpha-4/beta-1, Mucin 16/CA-125, RANKL, TNF alpha, VEGF-A, and other therapeutically advantageous targets.

In an aspect described herein is a method of treating cancer in a patient having a cancer characterized by a cancer antigen, said method comprising administering to said patient a therapeutically effective amount of a therapeutic antibody described herein. In certain embodiments, the patient is human.

In an aspect described herein is a method of treating immune disorders in a patient having an immune disorder characterized by an immune antigen, said method comprising administering to said patient a therapeutically effective polypeptide, antibody or protein described herein.

In an aspect is a pharmaceutical composition, said composition comprising a therapeutically effective amount of a polypeptide described herein, and a pharmaceutically acceptable carrier.

In an aspect described herein are polypeptides, said polypeptides comprising a variant Fc region with at least three amino acid substitutions, and wherein said polypeptides are more effective at mediating antibody-dependent cellular cytotoxicity (ADCC) relative to wild type. In certain embodiments, the polypeptide comprising a variant Fc region is about 1.5 to about 100 fold more effective in mediating ADCC relative to wild type. In certain embodiments, the polypeptide comprising a variant Fc region is about 2 to about 50 fold more effective in mediating ADCC relative to wild type.

In an aspect described herein are polypeptides, said polypeptides comprising a variant Fc region with at least three amino acid substitutions, wherein the polypeptide is more effective at mediating inhibition of inflammatory immune responses relative to wild type. In certain embodiments, the polypeptide comprising a variant Fc region is about 2 fold more effective in mediating inhibition of inflammatory immune responses relative to wild type. In some embodiments, the polypeptide comprising a variant Fc region is about 10 fold more effective in mediating inhibition of inflammatory immune responses relative to wild type. In certain embodiments, the polypeptide comprising a variant Fc region is about 50 fold more effective in mediating inhibition of inflammatory immune responses relative to wild type. In certain embodiments, the polypeptide comprising a variant Fc region is about 100 fold more effective in mediating inhibition of inflammatory immune responses relative to wild type.

Also provided herein is a method for identifying Fc variant polypeptides in silico based on calculated binding affinities to FcγRIIa, FcγRIIb and/or FcγRIIIa. In certain embodiments, the method of identifying Fc variant polypeptides in silico further calculates in silico electrostatics, solvation, packing, packing density, hydrogen binding, and entropic effects of said Fc variant polypeptides. In certain embodiments, the method of identifying Fc variant polypeptides in silico further comprises constructing the identified Fc variant polypeptides and expressing said polypeptides in the context of an antibody in mammalian cells.

Other aspects and features of the present invention will become apparent to those ordinarily skilled in the art upon review of the following description of specific embodiments of the invention.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
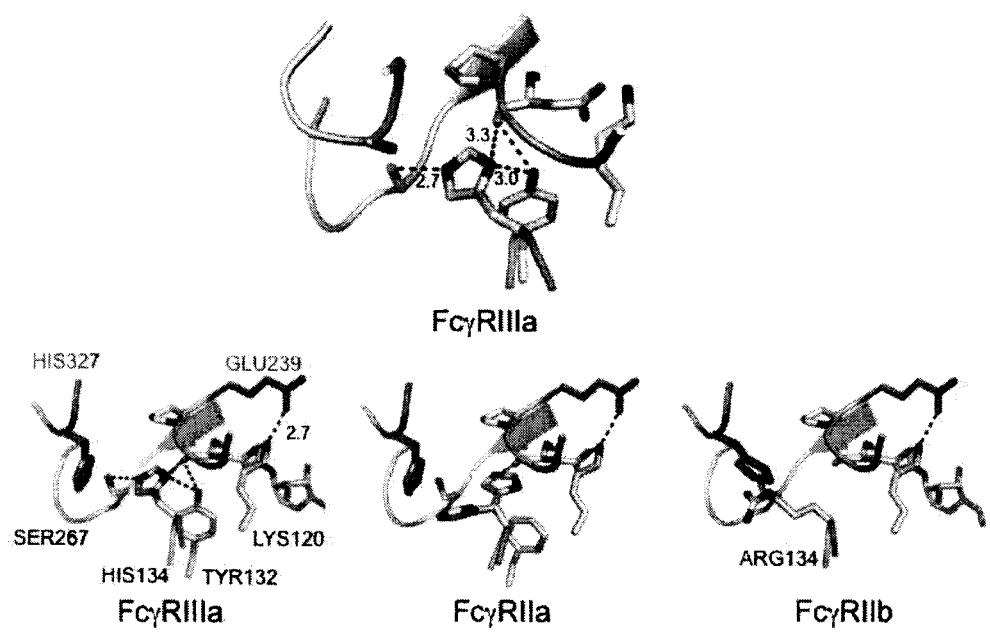
FIG. 1: Effects of the A327H and S239E mutations: A portion of the binding interface is shown between the chain-B of the antibody Fc (green) and the various Fcγ receptors (wheat). The wild-type Fc to FcγRIIIa structure is shown on top with Fc variant-induced changes in structure and dynamics for each receptor shown on the bottom. Side-chain positions to be mutated are colored in dark green and the residue labels are in red. Dashed lines denote electrostatic interactions with the distances shown in angstroms (Å). For the FcγRIIa, the two displayed conformations of His134 are the maximum allowable conformational movements with the intermediate conformers omitted for clarity.

Embodiments disclosed herein are drawn to polypeptides, fusion protein and antibodies comprising at least three substitutions in the Fc region wherein the polypeptide binds a target FcγR receptor with higher specificity compared to a polypeptide that lacks the at least three substitutions. These polypeptides and antibodies are designed by rational analysis of the binding of each FcγR with the Fc region and by subsequent design of multiple amino acid substitutions that synergistically provide enhanced selectivity and binding affinity for the target Fc receptor. Accordingly, the polypeptides and proteins provided herein comprise multiple variations in the Fc region as compared to the wild type Fc region, said variations tailored to improving the specificity for the FcγR under consideration, and for obtaining maximum energetically favorable binding based on enthalpic and entropic factors optimized by the choice of the most favorable amino acid for each substituted position.

One embodiment provides a polypeptide comprising a variant Fc region, wherein said variant Fc region comprises three or more amino acid modifications relative to a wild-type Fc region, and has an altered effect relative to a polypeptide comprising a wild-type Fc region; wherein at least two of the three or more modifications provide a synergistic effect compared to single position modifications at the at least two positions thereby exhibiting a selected binding profile to Fcγ receptors.

Another embodiment provides a polypeptide wherein the amino acid modifications produce amino acid interactions and dynamics that result in enhanced binding free energy to a first Fcγ receptor while diminishing binding affinity to a second Fcγ receptor compared to a polypeptide that lacks the at least three or more amino acid modifications. In certain embodiments, the first Fcγ receptor is FcγRIIIa receptor and the second Fcγ receptor is FcγRIIa or FcγRIIb.

Another embodiment provides a polypeptide wherein the amino acid modifications produce favorable FcγRIIIa-specific electrostatic interactions and steric repulsion to FcγRIIa and/or FcγRIIb receptors.

Another embodiment provides a polypeptide wherein the amino acid modifications have minimal impact on the FcγRIIIa receptor while producing detrimental effects on binding of the polypeptide to FcγRIIa and/or FcγRIIb.

Another embodiment provides a polypeptide of wherein the amino acid substitutions preserve the binding interface and the protein-protein interactions with the FcγRIIIa when compared to the wild-type Fc, and result in disruption of binding of the polypeptide to the FcγRIIa receptor is disrupted.

Any patent, application or other reference cited or repeated below, or above, is incorporated by references in its entirety for all purposes as well as for the proposition that is recited.

The following definitions may be used to understand the compositions and methods provided herein, but are meant to encompass scientific equivalents.

Throughout the present specification and claims, the numbering of the residues in an immunoglobulin heavy chain is that of the EU index as in Kabat et al., Sequences of Proteins of Immunological Interest, 5th Ed. Public Health Service, National Institutes of Health, Bethesda, Md. (1991), expressly incorporated herein by reference. The "EU index as in Kabat" refers to the residue numbering of the human IgG1 EU antibody.

A "parent polypeptide" is a polypeptide comprising an amino add sequence which lacks one or more of the Fc region modifications disclosed herein and which differs in effector function compared to a polypeptide variant as herein disclosed. The parent polypeptide may comprise a native sequence Fc region or an Fc region with pre-existing amino acid sequence modifications (such as additions, deletions and/or substitutions).

As used herein, "synergistic" means that the FcγR binding of the Fc protein designed with multiple amino acid substitutions is greater than their additive binding observed for individual substitutions.

The term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The Fc region of an immunoglobulin generally comprises two constant domains, CH2 and CH3.

The "CH2 domain" of a human IgG Fc region (also referred to as "Cγ2" domain) usually extends from about amino acid 231 to about amino acid 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, Molec. Immunol. 22:161-206 (1985).

The "CH3 domain" comprises the stretch of residues C-terminal to a CH2 domain in an Fc region (i.e. from about amino acid residue 341 to about amino acid residue 447 of an IgG)

A "functional Fc region" possesses an "effector function" of a native sequence Fc region. Exemplary "effector functions" include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays as herein disclosed, for example.

A "native sequence Fc region" comprises an amino add sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one "amino acid modification" as herein defined. The variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. In certain embodiments, the variant Fc region herein possesses at least about 80% homology with a native sequence Fc region and/or with an Fc region of a parent polypeptide, and most preferably at least about 90% homology therewith, more preferably at least about 95% homology therewith.

"Homology" is defined as the percentage of residues in the amino acid sequence variant that are identical after aligning the sequences and introducing gaps, if necessary, to achieve the maximum percent homology. Methods and computer programs for the alignment are well known in the art. One such computer program is "Align 2", authored by Genentech, Inc., which was filed with user documentation in the United States Copyright Office, Washington, D.C. 20559, on Dec. 10, 1991.

The term "Fc region-containing polypeptide" refers to a polypeptide, such as an antibody or immunoadhesin (see definitions below), which comprises an Fc region.

The terms "Fc receptor" or "FcR" are used to describe a receptor that binds to the Fc region of an antibody. The preferred FcR is a native sequence human FcR. Moreover, in certain embodiments, the FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daeron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future are encompassed by the term "FcR" herein. The term also includes the neonatal receptor, FcRn, which is responsible for the transfer of materal IgGs to the fetus (Guyer et al., J. Immunol. 117:587 (1976) and Kim et al., J. Immunol. 24:249 (1994)).

"Antibody-dependent cell-mediated cytotoxicity" and "ADCC" refer to a cell-mediated reaction in which nonspecific cytotoxic cells that express FcRs (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g. from blood or PBMCs as described herein.

A polypeptide with "altered" FcR binding affinity or ADCC activity is one which has either enhanced or diminished FcR binding activity and/or ADCC activity compared to a parent polypeptide or to a polypeptide comprising a native sequence Fc region. The polypeptide which "displays increased binding" to an FcR binds at least one FcR with better affinity than the parent polypeptide. The polypeptide which "displays decreased binding" to an FcR, binds at least one FcR with worse affinity than a parent polypeptide. Such variants which display decreased binding to an FcR may possess little or no appreciable binding to an FcR, e.g., 0-20% binding to the FcR compared to a native sequence IgG Fc region, e.g. as determined in the Examples herein.

The polypeptide which binds an FcR with "better affinity" than a parent polypeptide, is one which binds any one or more of the above identified FcRs with substantially better binding affinity than the parent antibody, when the amounts of polypeptide and parent polypeptide in the binding assay are essentially the same. For example, the polypeptide with improved FcR binding affinity may display from about 1.15 fold to about 100 fold, e.g. from about 1.2 fold to about 50 fold improvement in FcR binding affinity compared to the parent polypeptide, where FcR binding affinity is determined, for example, as disclosed in the Examples herein.

The polypeptide which "mediates antibody-dependent cell-mediated cytotoxicity (ADCC) in the presence of human effector cells more effectively" than a parent antibody is one which in vitro or in vivo is substantially more effective at mediating ADCC, when the amounts of polypeptide variant and parent antibody used in the assay are essentially the same. Generally, such polypeptides will be identified using the in vitro ADCC assay as herein disclosed, but other assays or methods for determining ADCC activity, e.g. in an animal model etc, are contemplated. The preferred polypeptide is from about 1.5 fold to about 100 fold, e.g. from about two fold to about fifty fold, more effective at mediating ADCC than the parent, e.g. in the in vitro assay disclosed herein.

An "amino acid modification" refers to a change in the amino acid sequence of a predetermined amino acid sequence. Exemplary modifications include an amino acid substitution, insertion and/or deletion. In certain embodiments the amino acid modification herein is a substitution.

An "amino acid modification at" a specified position, e.g. of the Fc region, refers to the substitution or deletion of the specified residue, or the insertion of at least one amino acid residue adjacent the specified residue. By insertion "adjacent" a specified residue is meant insertion within one to two residues thereof. In certain embodiments the insertion is N-terminal or C-terminal to the specified residue.

An "amino acid substitution" refers to the replacement of at least one existing amino acid residue in a predetermined amino acid sequence with another different "replacement" amino acid residue. The replacement residue or residues may be "naturally occurring amino acid residues" (i.e. encoded by the genetic code) and selected from the group consisting of: alanine (Ala); arginine (Arg); asparagine (Asn); aspartic acid (Asp); cysteine (Cys); glutamine (Gln); glutamic acid (Glu); glycine (Gly); histidine (His); Isoleucine (Ile): leucine (Leu); lysine (Lys); methionine (Met); phenylalanine (Phe); proline (Pro): serine (Ser); threonine (Thr); tryptophan (Trp); tyrosine (Tyr); and valine (Val). Preferably, the replacement residue is not cysteine. Substitution with one or more non-naturally occurring amino acid residues is also encompassed by the definition of an amino acid substitution herein. A "non-naturally occurring amino acid residue" refers to a residue, other than those naturally occurring amino acid residues listed above, which is able to covalently bind adjacent amino acid residues(s) in a polypeptide chain. Examples of non-naturally occurring amino acid residues include norleucine, ornithine, norvaline, homoserine and other amino acid residue analogues such as those described in Ellman et al. Meth. Enzym. 202:301-336 (1991). To generate such non-naturally occurring amino acid residues, the procedures of Noren et al. Science 244:182 (1989) and Ellman et al., supra, can be used. Briefly, these procedures involve chemically activating a suppressor tRNA with a non-naturally occurring amino acid residue followed by in vitro transcription and translation of the RNA.

An "amino acid insertion" refers to the incorporation of at least one amino acid into a predetermined amino acid sequence. In certain embodiments, the insertion consists of the insertion of one or two amino acid residues. In certain other embodiments, are larger "peptide insertions", e.g. insertion of about three to about five or even up to about ten amino acid residues. In these embodiments the inserted residue(s) are naturally occurring or non-naturally occurring as disclosed above.

An "amino acid deletion" refers to the removal of at least one amino acid residue from a predetermined amino acid sequence.

"Hinge region" is generally defined as stretching from Glu216 to Pro230 of human IgG1 (Burton, Molec. Immunol. 22:161-206 (1985)). Hinge regions of other IgG isotypes may be aligned with the IgG1 sequence by placing the first and last cysteine residues forming inter-heavy chain S—S bonds in the same positions.

The "lower hinge region" of an Fc region is normally defined as the stretch of residues immediately C-terminal to the hinge region, i.e. residues 233 to 239 of the Fc region. Prior to the present disclosure, FcγR binding was generally attributed to amino acid residues in the lower hinge region of an IgG Fc region.

"C1q" is a polypeptide that includes a binding site for the Fc region of an immunoglobulin. C1q together with two serine proteases, C1r and C1s, forms the complex C1, the first component of the complement dependent cytotoxicity (CDC) pathway. Human C1q can be purchased commercially from, e.g. Quidel, San Diego, Calif.

The term "binding domain" refers to the region of a polypeptide that binds to another molecule. In the case of an FcR, the binding domain can comprise a portion of a polypeptide chain thereof (e.g. the .alpha. chain thereof) which is responsible for binding an Fc region. One useful binding domain is the extracellular domain of an FcRα chain.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

"Antibody fragments", as defined herein, comprise a portion of an intact antibody, generally including the antigen binding or variable region of the intact antibody or the Fc region of an antibody which retains FcR binding capability. Examples of antibody fragments include linear antibodies; single-chain antibody molecules; and multispecific antibodies formed from antibody fragments. In certain embodiments, the antibody fragments retain at least part of the hinge and optionally the CH1 region of an IgG heavy chain. In some embodiments the antibody fragments retain the entire constant region of an IgG heavy chain, and include an IgG light chain.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal," indicates the character of the antibody as being obtained from a substantially homogeneous population of antibodies, and is not to be construed as requiring production of the antibody by any particular method. In certain embodiments the monoclonal antibodies to be used in accordance with the present disclosure are made by the hybridoma method first described by Kohler et al., Nature 256:495 (1975), or may be made by recombinant DNA methods (see, e.g., U.S. Pat. No. 4,816,567). In some embodiments "monoclonal antibodies" are isolated from phage antibody libraries using the techniques described in Clackson et al., Nature 352:624-628 (1991) and Marks et al., J. Mol. Biol. 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human Immunoglobulin. For further details, see Jones et al., Nature 321:522-525 (1986); Riechmann et al., Nature 332:323-329 (1988); and Presta, Curr. Op. Struct. Biol. 2:593-596 (1992).

The term "hypervariable region" when used herein refers to the amino acid residues of an antibody which are responsible for antigen-binding. The hypervariable region comprises amino acid residues from a "complementarity determining region" or "CDR" (ie. residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). "Framework" or "FR" residues are those variable domain residues other than the hypervariable region residues as herein defined.

As used herein, the term "immunoadhesin" designates antibody-like molecules which combine the "binding domain" of a heterologous "adhesin" protein (e.g. a receptor, ligand or enzyme) with an immunoglobulin constant domain. Structurally, the immunoadhesins comprise a fusion of the adhesin amino acid sequence with the desired binding specificity which is other than the antigen recognition and binding site (antigen combining site) of an antibody (i.e. is "heterologous") and an immunoglobulin constant domain sequence.

The term "ligand binding domain" as used herein refers to any native cell-surface receptor or any region or derivative thereof retaining at least a qualitative ligand binding ability of a corresponding native receptor. In a specific embodiment, the receptor is from a cell-surface polypeptide having an extracellular domain that is homologous to a member of the immunoglobulin supergenefamily. Other receptors, which are not members of the immunoglobulin supergenefamily but are nonetheless specifically covered by this definition, are receptors for cytokines, and in particular receptors with tyrosine kinase activity (receptor tyrosine kinases), members of the hematopoietin and nerve growth factor receptor superfamilies, and cell adhesion molecules, e.g. (E-, L- and P-) selectins.

The term "receptor binding domain" is used to designate any native ligand for a receptor, including cell adhesion molecules, or any region or derivative of such native ligand retaining at least a qualitative receptor binding ability of a corresponding native ligand. This definition, among others, specifically includes binding sequences from ligands for the above-mentioned receptors.

An "antibody-immunoadhesin chimera" comprises a molecule that combines at least one binding domain of an antibody (as herein defined) with at least one immunoadhesin (as defined in this application). Exemplary antibody-immunoadhesin chimeras are the bispecific CD4-IgG chimeras described in Berg et al., PNAS (USA) 88:4723-4727 (1991) and Chamow et al., J. Immunol. 153:4268 (1994).

An "isolated" polypeptide is one that has been identified and separated and/or recovered from a component of its natural environment. Contaminant components of its natural environment are materials that would interfere with diagnostic or therapeutic uses for the polypeptide, and may include enzymes, hormones, and other proteinaceous or nonproteinadeous solutes. In certain embodiments, the polypeptide will be purified (1) to greater than 95% by weight of polypeptide as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated polypeptide includes the polypeptide in situ within recombinant cells since at least one component of the polypeptide's natural environment will not be present. Ordinarily, however, isolated polypeptide will be prepared by at least one purification step.

"Treatment" refers to both therapeutic treatment and prophylactic or preventative measures. Those in need of treatment include those already with the disorder as well as those in which the disorder is to be prevented.

A "disorder" is any condition that would benefit from treatment with the polypeptide variant. This includes chronic and acute disorders or diseases including those pathological conditions which predispose the mammal to the disorder in question. In one embodiment, the disorder is cancer.

The word "label" when used herein refers to a detectable compound or composition which is conjugated directly or indirectly to the polypeptide. In certain embodiments the label is itself detectable (e.g., radioisotope labels or fluorescent labels). In some other embodiments, the label catalyzes chemical alteration of a substrate compound or composition which is detectable. An exemplary embodiment comprises an enzymatic label that catalyzes a chemical alteration of a substrate compound or composition which is detectable.

An "isolated" nucleic acid molecule is a nucleic acid molecule that is identified and separated from at least one contaminant nucleic acid molecule with which it is ordinarily associated in the natural source of the polypeptide nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the polypeptide where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

The term "molecular complex" when used herein refers to the relatively stable structure which forms when two or more heterologous molecules (e.g. polypeptides) bind (preferably noncovalently) to one another. The preferred molecular complex herein is an immune complex.

"Immune complex" refers to the relatively stable structure which forms when at least one target molecule and at least one heterologous Fc region-containing polypeptide bind to one another forming a larger molecular weight complex. Examples of immune complexes are antigen-antibody aggregates and target molecule-immunoadhesin aggregates. The term "immune complex" as used herein, unless indicated otherwise, refers to an ex vivo complex (i.e. other than the form or setting in which it may be found in nature). However, the immune complex may be administered to a mammal, e.g. to evaluate clearance of the immune complex in the mammal.

The term "target molecule" refers to a molecule, usually a polypeptide, which is capable of being bound by a heterologous molecule and has one or more binding sites for the heterologous molecule. The term "binding site" refers to a region of a molecule to which another molecule can bind. The "first target molecule" herein comprises at least two distinct binding sites (for example, two to five separate binding sites) for an analyte (e.g. an Fc region-containing polypeptide) such that at least two analyte molecules can bind to the first target molecule. In a preferred embodiment, the two or more binding sites are identical (e.g. having the same amino acid sequence, where the target molecule is a polypeptide). An "analyte" is a substance that is to be analyzed. The preferred analyte is an Fc region-containing polypeptide that is to be analyzed for its ability to bind to an Fc receptor.

A "receptor" is a polypeptide capable of binding at least one ligand. The preferred receptor is a cell-surface receptor having an extracellular ligand-binding domain and, optionally, other domains (e.g. transmembrane domain, intracellular domain and/or membrane anchor). The receptor to be evaluated in the assay described herein may be an intact receptor or a fragment or derivative thereof (e.g. a fusion protein comprising the binding domain of the receptor fused to one or more heterologous polypeptides). Moreover, the receptor to be evaluated for its binding properties may be present in a cell or isolated and optionally coated on an assay plate or some other solid phase.

The phrase "low affinity receptor" denotes a receptor that has a weak binding affinity for a ligand of interest, e.g. having a binding constant of about 50 nM or worse affinity. Exemplary low affinity receptors include FcγRII and FcγRIII.

By "effector function" as used herein is meant a biochemical event that results from the interaction of an antibody Fc region with an Fc receptor or ligand. Effector functions include but are not limited to ADCC, ADCP, and CDC. By "effector cell" as used herein is meant a cell of the immune system that expresses one or more Fc receptors and mediates one or more effector functions. Effector cells include but are not limited to monocytes, macrophages, neutrophils, dendritic cells, eosinophils, mast cells, platelets, B cells, large granular lymphocytes, Langerhans' cells, natural killer (NK) cells, and γγ T cells, and may be from any organism including but not limited to humans, mice, rats, rabbits, and monkeys. By "library" herein is meant a set of Fc proteins in any form, including but not limited to a list of nucleic acid or amino acid sequences, a list of nucleic acid or amino acid substitutions at variable positions, a physical library comprising nucleic acids that encode the library sequences, or a physical library comprising the Fc protein proteins, either in purified or unpurified form.

By "Fc-fusion" as used herein is meant a protein wherein one or more polypeptides is operably linked to an Fc region or a derivative thereof. Fc fusion is herein meant to be synonymous with the terms "immunoadhesin", "Ig fusion", "Ig chimera", and "receptor globulin" (sometimes with dashes) as used in the prior art (Chamow et al., 1996, Trends Biotechnol 14:52-60; Ashkenazi et al., 1997, Curr Opin Immunol 9:195-200). An Fc fusion combines the Fc region of an immunoglobulin with a fusion partner, which in general can be any protein or small molecule. The role of the non-Fc part of an Fc fusion, i.e. the fusion partner, is to mediate target binding, and thus it is functionally analogous to the variable regions of an antibody. Virtually any protein or small molecule may be linked to Fc to generate an Fc fusion. Protein fusion partners may include, but are not limited to, the target-binding region of a receptor, an adhesion molecule, a ligand, an enzyme, a cytokine, a chemokine, or some other protein or protein domain. Small molecule fusion partners may include any therapeutic agent that directs the Fc fusion to a therapeutic target. Such targets may be any molecule, preferrably an extracellular receptor, that is implicated in disease. Two families of surface receptors that are targets of a number of approved small molecule drugs are G-Protein Coupled Receptors (GPCRs), and ion channels, including K+, Na+, Ca+ channels. Nearly 70% of all drugs currently marketed worldwide target GPCRs. Thus the Fc proteins described herein may be fused to a small molecule that targets, for example, one or more GABA receptors, puringeric receptors, adrenergic receptors, histaminergic receptors, opiod receptors, chemokine receptors, glutamate receptors, nicotinic receptors, the 5HT (serotonin) receptor, and estrogen receptors. A fusion partner may be a small-molecule mimetic of a protein that targets a therapeutically useful target. Specific examples of particular drugs that may serve as Fc fusion partners can be found in L. S. Goodman et at, Eds., Goodman and Gilman's The Pharmacological Basis of Therapeutics (McGraw-Hill, New York, ed. 9, 1996). Fusion partners include not only small molecules and proteins that bind known targets for existing drugs, but orphan receptors that do not yet exist as drug targets. The completion of the genome and proteome projects are proving to be a driving force in drug discovery, and these projects have yielded a trove of orphan receptors. There is enormous potential to validate these new molecules as drug targets, and develop protein and small molecule therapeutics that target them. Such protein and small molecule therapeutics are contemplated as Fc fusion partners that employ the Fc proteins described herein. A variety of linkers, defined and described below, may be used to covalently link Fc to a fusion partner to generate an Fc fusion.

By "Fc ligand" as used herein is meant a molecule, preferably a polypeptide, from any organism that binds to the Fc region of an antibody to form an Fc-ligand complex. Fc ligands include but are not limited to FcγRs, FcγRs, FcγRs, FcRn, C1q, C3, mannan binding lectin, mannose receptor, staphylococcal protein A, streptococcal protein G, and viral FcγR. Fc ligands also include Fc receptor homologs (FcRH), which are a family of Fc receptors that are homologous to the FcγRs (Davis et al., 2002, Immunological Reviews 190:123-136). Fc ligands may include undiscovered molecules that bind Fc.

By "IgG" as used herein is meant a polypeptide belonging to the class of antibodies that are substantially encoded by a recognized immunoglobulin gamma gene. In humans this class comprises IgG1, IgG2, IgG3, and IgG4. In mice this class comprises IgG1, IgG2a, IgG2b, IgG3. By "immunoglobulin (Ig)" herein is meant a protein consisting of one or more polypeptides substantially encoded by immunoglobulin genes. Immunoglobulins include but are not limited to antibodies. Immunoglobulins may have a number of structural forms, including but not limited to full length antibodies, antibody fragments, and individual immunoglobulin domains. By "immunoglobulin (Ig) domain" herein is meant a region of an immunoglobulin that exists as a distinct structural entity as ascertained by one skilled in the art of protein structure. Ig domains typically have a characteristic .quadrature.-sandwich folding topology. The known Ig domains in the IgG class of antibodies are $V_H$, $C\gamma1$, $C\gamma2$, $C\gamma3$, $V_L$, and $C_L$.

By "parent polypeptide" or "precursor polypeptide" (including Fc parent or precursors) as used herein is meant a polypeptide that is subsequently modified to generate a variant. Said parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it. Accordingly, by "parent Fc polypeptide" as used herein is meant an unmodified Fc polypeptide that is modified to generate a variant, and by "parent antibody" as used herein is meant an unmodified antibody that is modified to generate a variant antibody.

By "residue" as used herein is meant a position in a protein and its associated amino acid identity. For example, Asparagine 297 (also referred to as Asn297, also referred to as N297) is a residue in the human antibody IgG1.

By "target antigen" as used herein is meant the molecule that is bound specifically by the variable region of a given antibody. A target antigen may be a protein, carbohydrate, lipid, or other chemical compound.

By "target cell" as used herein is meant a cell that expresses a target antigen.

By "variable region" as used herein is meant the region of an immunoglobulin that comprises one or more Ig domains substantially encoded by any of the Vκ, Vλ, and/or $V_H$ genes that make up the κ, λ, and heavy chain immunoglobulin genetic loci respectively.

By "variant polypeptide" as used herein is meant a polypeptide sequence that differs from that of a parent polypeptide sequence by virtue of at least one amino acid modification. Variant polypeptide may refer to the polypeptide itself, a composition comprising the polypeptide, or the amino sequence that encodes it. Preferably, the variant polypeptide has at least one amino acid modification compared to the parent polypeptide, e.g. from about one to about ten amino acid modifications, and preferably from about one to about five amino acid modifications compared to the parent. The variant polypeptide sequence herein will preferably possess at least about 80% homology with a parent polypeptide sequence, and most preferably at least about 90% homology, more preferably at least about 95% homology. Accordingly, by "Fc protein" as used herein is meant an Fc sequence that differs from that of a parent Fc sequence by virtue of at least one amino acid modification. An Fc protein may only encompass an Fc region, or may exist in the context of an antibody, Fc fusion, or other polypeptide that is substantially encoded by Fc. Fc protein may refer to the Fc polypeptide itself, compositions comprising the Fc protein polypeptide, or the amino acid sequence that encodes it. In an exemplary embodiment, the variant proteins described herein comprise an Fc protein, as described herein, and as such, may comprise an antibody (and the corresponding derivatives) with the Fc protein, or an Fc fusion protein that comprises the Fc protein. In addition, in some cases, the Fc is a variant as compared to a wild-type Fc, or to a "parent" variant.

The term "Antibody-Dependent Cell-Mediated Cytotoxicity" (ADCC) refers to a mechanism of cell-mediated immunity whereby an effector cell of the immune system actively lyses a target cell that has been bound by specific antibodies. The Fc region Variant polypeptides and proteins described herein successfully modulate ADCC as compared to the wild type Fc region antibodies. In certain embodiments, the Variant polypeptide results in reduced ADCC as compared to the wild-type Fc region. In certain other embodiments, the Fc region Variant described herein results in increased ADCC as compared to the corresponding wild-type Fc region.

The term geometric metrics describes the plurality of measurable physical attributes of a structural unit or residue (used interchangeably herein) of a biopolymer, an amino acid in the case of a protein. Geometric metrics can be defined either by 1) dihedral, plane or other measurable angles as defined by the atoms of the respective residue, 2) distances between atoms of the same residue or to atoms of another residue, and/or 3) distance between atoms of the same residue and a reference atom or position in the structure.

A residue population is the sum of all snapshots or samples obtained for a single residue. In certain embodiments the population is equal to the number of frames captured in a molecular dynamics simulation or the number of samples taken from a Monte Carlo simulation.

A residue conformation is defined in terms of the observed combination of geometric metrics attributed to a particular residue structure. A residue cluster refers to the plurality of snapshots, which have been assigned the same conformation, based on clustering all or a part of the defined geometric metrics. A conformational frequency refers to the number of frames which have been assigned the same residue conformation.

Simulation refers to the process of conformational sampling, performed either by either molecular dynamics or a Monte Carlo based sampling approach. A trajectory contains the conformational frames produced by a simulation. Graph theory refers to the term as used in mathematics and computer science (for example, see Reinhard Diestel, Graph Theory; Edition 3, Springer 2005).

The term clustering tools refers to the plurality of mathematical methods and algorithms and programs which implement those, that can be used to identify clusters of similar data points from data sets.

The term Dynamical Cross Correlation Method refers to a graphical representation of the cross correlation matrix of atomic displacements of a molecular structure in a molecular dynamics trajectory with reference to another conformational state of that structure.

Normal mode analysis is the study of characteristic harmonic vibrations and frequencies about a local energy minimum of a molecular system.

Elastic network model refers to the representation of a protein structure as comprising of a network of harmonic springs approximating the interaction between residue pairs.

Provided herein are polypeptides comprising a variant Fc region, wherein said variant Fc region comprises at least three amino acid modifications relative to a wild-type Fc region, and has an altered effect relative to a polypeptide comprising a wild-type Fc region or variant Fc region comprising only one or two amino acid modifications; and wherein at least two of the modifications provide a synergistic effect compared to single position modifications thereby exhibiting a selected binding profile to Fcγ receptors. In certain embodiments, one or both amino acid modifications are located between positions 234-330 according to the EU index. In certain embodiments, the modifications do not comprise simultaneous substitution at positions 317 and 353 according to the EU index. In some embodiments, the amino acid modifications do not comprise a substitution at position 332 according to the EU index. In certain embodiments, the polypeptides comprise the modifications L235A/S239E/D265E. In some embodiments, the polypeptides comprise the modifications A327H/E269L/K236A. In one embodiment, the polypeptides comprise the modifications G237F/D270Q/S239E. In some other embodiments, the polypeptides comprise the modifications A330V/I332L/K326. In one embodiment, the polypeptides comprise the modifications G236S/A327H/A330I.

In certain embodiments of the polypeptides described herein, the amino acid modifications produce amino acid interactions and dynamics that result in enhanced binding affinity and/or specificity to a first Fcγ receptor while diminishing binding affinity and/or specificity to a second Fcγ receptor compared to a polypeptide that lacks the three or more amino acid modifications. In some of these embodiments, the first Fcγ receptor is FcγRIIIa receptor and the second Fcγ receptor is FcγRIIa or FcγRIIb. In certain embodiments, the amino acid modifications produce favorable FcγRIIIa-specific interactions and/or unfavorable interactions with FcγRIIa and/or FcγRIIb receptors. In some embodiments, the amino acid modifications have minimal impact on the FcγRIIIa receptor while producing detrimental effects on binding of the polypeptide to FcγRIIa and/or FcγRIIb.

Provided herein are polypeptides comprising a variant Fc region, wherein said variant Fc region comprises at least three amino acid modifications relative to a wild-type Fc region, wherein the amino acid modifications produce amino acid interactions and dynamics that result in enhanced binding affinity and/or specificity to a FcγRIIIa receptor while diminishing binding affinity and/or specificity to FcγRIIa or FcγRIIb receptor compared to a polypeptide that lacks the two amino acid modifications. In some embodiments, the polypeptide comprises modifications S239E/D265S/I332E. In certain embodiments, the polypeptide comprises the modifications G237F/S239E/A327H. In certain other embodiments, the polypeptide comprises modifications H268D/E269L/S298A/K326A/A327H. In some embodiments, the polypeptide comprises the modifications L235A/S239E/D265E/A327H. In an embodiment, the polypeptide comprises the modifications G237F/S239E/D270N. In some embodiments, the polypeptide comprises the modifications G236E/G237F/S239E. In an embodiment, the polypeptide comprises the modifications S239E/D265SI332E and alternatively H268D. In certain embodiments, the polypeptide comprises modifications selected from the group of G237F/S239E/D265E, S239E/S298A/K326A/A327H, and G236E/D270N/A327V/I332E. In certain embodiments, the polypeptide comprises the modifications S298A/K326A/A327H wherein the polypeptide has improved binding selectivity to FcγRIIIa receptor as compared to a polypeptide lacking the S298A/K326A/A327H modifications.

In an aspect, provided herein are polypeptides comprising a variant Fc region, wherein said variant Fc region comprises at least three amino acid modifications relative to a wild-type Fc region, wherein the amino acid modifications produce amino acid interactions and dynamics that result in enhanced binding affinity and/or specificity to a FcγRIIa receptor while diminishing binding affinity and/or specificity to FcγRIIIa or FcγRIIb receptor compared to a polypeptide that lacks at least one of the amino acid modifications. In some embodiments, the polypeptide comprises modifications G237F, A327L and A330I. In certain embodiments, the amino acid modifications produce favorable FcγRIIa-specific interactions and/or unfavorable interactions with FcγRIIIa and/or FcγRIIb receptors. In certain embodiments, the amino acid modifications have minimal impact on the FcγRIIa receptor while producing detrimental effects on binding of the polypeptide to FcγRIIIa and/or FcγRIIb. In certain embodiments, the polypeptide comprises modifications G237F, S239E and H268D. In some embodiments, the polypeptide comprises modifications D265E/S267D/A330S.

In a further aspect, provided herein are polypeptides comprising a variant Fc region, wherein said variant Fc region comprises at least three amino acid modifications relative to a wild-type Fc region, wherein the amino acid modifications produce amino acid interactions and dynamics that result in enhanced binding affinity and/or specificity to a FcγRIIb receptor while diminishing binding affinity and/or specificity to FcγRIIIa or FcγRIIa receptor compared to a polypeptide that lacks at least one of the amino acid modifications. In certain embodiments, the amino acid modifications produce favorable FcγRIIb-specific interactions and/or unfavorable interactions with FcγRIIIa and/or FcγRIIa receptors. In certain embodiments, the amino acid modifications have minimal impact on the FcγRIIb receptor while producing detrimental effects on binding of the polypeptide to FcγRIIIa and/or FcγRIIa. In certain embodiments, the polypeptide comprises modifications S239D/D265S/S298A/I332E. In some other embodiments, the polypeptide comprises the modifications G237F/S298A/A330L/I332E. In some embodiments the polypeptide comprises the modifications H268D, K326A, A327H and alternatively one or both of E269L and S298A. In an embodiment, the polypeptide comprises the modifications G237F/V266L/S267D. In some embodiments, the polypeptides comprise the modifications L234F/S267G/N325L or L234F/S267E/N325L. In an embodiment, the polypeptide comprises modifications G236A/S239D/D270L/I332E.

In certain aspects described herein, the binding of the polypeptide comprising a wild-type Fc region to Fcγ receptors is detectable by an in vitro assay.

In an aspect, provided herein are polypeptides comprising a variant Fc region, wherein said variant Fc region comprises at least three amino acid modifications relative to a wild-type Fc region, wherein one of the modifications comprises the mutation S239E wherein the polypeptide has higher selectivity in binding to the FcγRIIIa receptor compared to a polypeptide that lacks the S239E mutation.

In an aspect, provided herein are polypeptides comprising a variant Fc region, wherein said variant Fc region comprises at least three amino acid modifications relative to a wild-type Fc region, wherein one of the modifications comprises the mutation S239E one of the modifications comprises the mutation S298A wherein the polypeptide has reduced binding affinity to FcγRIIa and FcγRIIb receptors compared to a polypeptide that lacks the S298A mutation.

In an aspect provided herein are polypeptides comprising a variant Fc region, wherein said variant Fc region comprises at least three amino acid modifications relative to a wild-type Fc region, said modifications selected from D270L/Y300L/A330K, G237F/S267G/N325F, G237F/V266L/S267D, L234F/S267G/N325L, L234F/S267E/N325L, G237F/S239E/A327H, G237F/A327L/A330I, S239E/A327L/A330I, S239E/S267E/H268D, G237F/S239E/D270N, G236E/G237F/S239E, S239E/D265S/I332E, G237F/S239E/D265E, G237F/S239E/H268D, H268E/D270E/S267G, H268D/K326A/A327H, D265E/S267D/A330S, L235A/S239E/D265E, A327H/E269L/K236A, G237F/D270Q/S239E, A330V/I332L/K326, and G236S/A327H/A330I.

In an aspect provided herein are polypeptides comprising a variant Fc region, wherein said variant Fc region comprises at least four amino acid modifications relative to a wild-type Fc region, said modifications selected from L235A/S239E/D265E/A327H, S239E/D265S/H268D/I332E, S239D/D265S/S298A/I332E, S239E/S298A/K326A/A327H, G237F/S298A/A330L/I332E, and G236E/D270N/A327V/I332E, G236A/S239D/D270L/I332E and H268D/E269L/S298A/K326A/A327H.

In an aspect provided herein are polypeptides comprising a variant Fc region, wherein said variant Fc region comprises at least three amino acid modifications relative to a wild-type Fc region, wherein the at least three amino acid modifications are selected from the group consisting of: L234Q, L234N, L235A, G236E, E236L, E236D, G237F, G237N, S239E, S239D, D265E, D265S, S267E, S267D, S267G, H268D, H268E, E269L, E269L, D270N, D270I, D270E, S298A, K326A, K326D, A327H, A327V, A327L, A327T, A330V, A330L, A330W, A330I, A330S, I332L, I332D, and I332E.

In an aspect provided herein are polypeptides comprising a variant Fc region, said variant Fc region comprises a combination of amino acid modifications wherein said combination is selected from the group consisting of: L235A/S239E/D265E; L235A/G237F/D265E; S239E/E269D/A327H; S239E/G237N/A327H; S239E/G237F/A327V; G237F/D270I/S239E; G237F/A327L/S239E; A327H/E269L/K326A; A330V/I332L/S239E; A327T/E269L/K326A; D270N/A327T/K326A; A330V/I332L/S239E; A330W/I332D/S239E; G236E/D265E/A327H/A330I; D270N/S298A/A327V; G236E/D265E/D270N/A327H/A330I; G236E/D270N/A327H/A330I; G236E/D270N/A327V/I332E; G236E/D270N/A327V/G237F; L234N/S239E/A330I/I332E; L234Q/S239E/A330I/I332E; L234Q/S239E/A330I/I332E/S298A; G237F/S239D/D265E/D270N/S298A; G237F/S239E/D270N/A330L/I332E; G237F/S239E/D270N/A330L/I332E/S298A; S239E/G237F/A327H; G237F/A327L/A330I; S239E/A330I/A327L; D265E/S239E/L235A/A327H; S267E/S239E/H268D; G237F/D270N/S239E; S239E/G237F/G236E; I332E/D265S/S239E/H268D; I332E/D265S/S239E; D265E/S239E/G237F; S239E/H268D/G237F; S298A/D265S/S239D/I332E; S298A/K326A/A327H/S239E; S298A/G237F/A330L/I332E; H268E/D270E/S267G; H268D/K326A/A327H; H268D/K326A/A327H/E269L/S298A; A330S/D265E/S267D; S239E/S267E/H268D; S237F/S239E/D265E and H268E/D270/E/S267G In an aspect, provided herein are polypeptides that comprise a variant Fc region, wherein said variant Fc region comprises at least three amino acid modifications relative to a wild-type Fc region wherein when said variant Fc region comprises amino acid modification H268D, said variant does not comprise the modification S267E.

In certain embodiments of the polypeptides described herein, the Fc region of the parent polypeptide is a human IgG Fc region. In some of these embodiments, the human IgG Fc region is a human IgG1, IgG2, IgG3, or IgG4 Fc region.

In certain embodiments of the polypeptides described herein, the polypeptide is an antibody. In some embodiments, the antibody is a monoclonal antibody, a humanized antibody, or a human antibody.

In an aspect is a nucleic acid comprising: a nucleotide sequence encoding a polypeptide described herein. In certain embodiments is a vector, comprising the nucleic acid.

In an aspect is a method for producing a polypeptide or protein described herein, said method comprising: (i) culturing in a medium a host cell comprising a nucleic acid encoding said polypeptide, under conditions suitable for the expression of said polypeptide; and (ii) recovering the polypeptide from said medium.

In an aspect described herein is a therapeutic antibody that specifically binds a cancer target antigen, said therapeutic antibody comprising a variant Fc region polypeptide described herein. In certain embodiments, the therapeutic antibody is selected from the group consisting of abagovomab, adalimumab, alemtuzumab, aurograb, bapineuzumab, basiliximab, belimumab, bevacizumab, briakinumab, canakinumab, catumaxomab, certolizumab pegol, cetuximab, daclizumab, denosumab, efalizumab, galiximab, gemtuzumab ozogamicin, golimumab, ibritumomab tiuxetan, infliximab, ipilimumab, lumiliximab, mepolizumab, motavizumab, muromonab, mycograb, natalizumab, nimotuzumab, ocrelizumab, ofatumumab, omalizumab, palivizumab, panitumumab, pertuzumab, ranibizumab, reslizumab, rituximab, teplizumab, tocilizumab/atlizumab, tositumomab, trastuzumab, Proxinium™, Rencarex™, ustekinumab, zalutumumab, and any other antibodies. In certain embodiments, the target antigen is selected from the group consisting of a-chain (CD25) of IL-2R, Amyloid beta, anti-EpCAM×anti-CD3, BLyS (or BAFF), CD11a, CD20, CD22, CD23, CD3, CD4, CD52, CD80, CTLA-4, EGFR, EpCAM, F protein of RSV, G250, glycoprotein IIb/IIIa R, HER2, HER2/neu R, Hsp90, IgE antibody, IL-12/IL-23, IL-1b, IL-5, IL-6 receptor, Integrin alpha-4/beta-1, Mucin 16/CA-125, RANKL, TNF alpha, VEGF-A, and other therapeutically advantageous targets.

In an aspect described herein is a method of treating cancer in a patient having a cancer characterized by a cancer antigen, said method comprising administering to said patient a therapeutically effective amount of a therapeutic antibody described herein. In certain embodiments, the patient is human.

In an aspect described herein is a method of treating immune disorders in a patient having an immune disorder characterized by an immune antigen, said method comprising administering to said patient a therapeutically effective polypeptide, antibody or protein described herein.

In an aspect is a pharmaceutical composition, said composition comprising a therapeutically effective amount of a polypeptide described herein, and a pharmaceutically acceptable carrier.

In an aspect described herein are polypeptides, said polypeptides comprising a variant Fc region with at least three amino acid substitutions, and wherein said polypeptides are more effective at mediating antibody-dependent cellular cytotoxicity (ADCC) relative to wild type. In certain embodiments, the polypeptide comprising a variant Fc region is about 1.5 to about 100 fold more effective in mediating ADCC relative to wild type. In certain embodiments, the polypeptide comprising a variant Fc region is about 2 to about 50 fold more effective in mediating ADCC relative to wild type.

In an aspect described herein are polypeptides, said polypeptides comprising a variant Fc region with at least three amino acid substitutions, wherein the polypeptide is more effective at mediating inhibition of inflammatory immune responses relative to wild type. In certain embodiments, the polypeptide comprising a variant Fc region is about 2 fold more effective in mediating inhibition of inflammatory immune responses relative to wild type. In some embodiments, the polypeptide comprising a variant Fc region is about 10 fold more effective in mediating inhibition of inflammatory immune responses relative to wild type. In certain embodiments, the polypeptide comprising a variant Fc region is about 50 fold more effective in mediating inhibition of inflammatory immune responses relative to wild type. In certain embodiments, the polypeptide comprising a variant Fc region is about 100 fold more effective in mediating inhibition of inflammatory immune responses relative to wild type.

Also provided herein is a method for identifying Fc variant polypeptides in silico based on calculated binding affinities to FcγRIIa, FcγRIIb and/or FcγRIIIa. In certain embodiments, the method of identifying Fc variant polypeptides in silico further calculates in silico electrostatics, solvation, packing, packing density, hydrogen binding, and entropic effects of said Fc variant polypeptides. In certain embodiments, the method of identifying Fc variant polypeptides in silico further comprises constructing the identified Fc variant polypeptides and expressing said polypeptides in the context of an antibody in mammalian cells.

The Fc polypeptides and proteins described herein may be optimized for a variety of properties. Properties that may be optimized include but are not limited to enhanced or reduced affinity for an FcγR. In a preferred embodiment, the Fc proteins described herein are optimized to possess enhanced affinity for a human activating FcγRI, preferably FcγRII, FcγRIIa, FcγRIIc, FcγRIIIa, and FcγRIIIb, most preferably FcγRIIIa. In an alternately preferred embodiment, the Fc proteins are optimized to possess reduced affinity for the human inhibitory receptor FγRIIb. These preferred embodiments are anticipated to provide antibodies and Fc fusions with enhanced therapeutic properties in humans, for example enhanced effector function and greater anti-cancer potency. In an alternate embodiment, the Fc proteins described herein are optimized to have reduced or ablated affinity for a human FcγRI, including but not limited to FcγRII, FcγRIIa, FcγRIIb, FcγRIIc, FcγRIIIa, and FcγRIIIb. These embodiments are anticipated to provide antibodies and Fc fusions with enhanced therapeutic properties in humans, for example reduced effector function and reduced toxicity. Preferred embodiments comprise optimization of Fc binding to a human FcγR, however in alternate embodiments the Fc polypeptides and proteins of the present invention possess enhanced or reduced affinity for FcγRs from nonhuman organisms, including but not limited to mice, rats, rabbits, and monkeys. Fc proteins that are optimized for binding to a nonhuman FcγR may find use in experimentation. For example, mouse models are available for a variety of diseases that enable testing of properties such as efficacy, toxicity, and pharmacokinetics for a given drug candidate. As is known in the art, cancer cells can be grafted or injected into mice to mimic a human cancer, a process referred to as xenografting. Testing of antibodies or Fc fusions that comprise Fc proteins that are optimized for one or more mouse FcγRs, may provide valuable information with regard to the efficacy of the antibody or Fc fusion, its mechanism of action, and the like. In certain embodiments, the Fc polypeptides and proteins described herein are optimized for enhanced functionality and/or solution properties in aglycosylated form. In an exemplary embodiment, the aglycosylated Fc proteins described herein bind an Fc ligand with greater affinity than the aglycosylated form of the parent Fc polypeptide. Said Fc ligands include but are not limited to FcγRs, C1q, FcRn, and proteins A and G, and may be from any source including but not limited to human, mouse, rat, rabbit, or monkey, preferably human. In an alternately preferred embodiment, the Fc proteins are optimized to be more stable and/or more soluble than the aglycosylated form of the parent Fc polypeptide. An Fc protein that is engineered or predicted to display any of the aforementioned optimized properties is herein referred to as an "optimized Fc protein".

In certain embodiments, the Fc polypeptides and proteins described herein are derived from parent Fc polypeptides that are themselves from a wide range of sources. In some embodiments the parent Fc polypeptide is substantially encoded by one or more Fc genes from any organism, including but not limited to humans, mice, rats, rabbits, camels, llamas, dromedaries, monkeys, preferably mammals and most preferably humans and mice. In an embodiment, the parent Fc polypeptide comprises an antibody, referred to as the parent antibody. In certain embodiments, the parent antibody is fully human, obtained for example using transgenic mice (Bruggemann et al., 1997, Curr Opin Biotechnol 8:455-458) or human antibody libraries coupled with selection methods (Griffiths et al., 1998, Curr Opin Biotechnol 9:102-108). The parent antibody need not be naturally occurring. In certain embodiments the parent antibody is an engineered antibody, including but not limited to chimeric antibodies and humanized antibodies (Clark, 2000, Immunol Today 21:397-402). In certain embodiments, the parent antibody is an engineered variant of an antibody that is substantially encoded by one or more natural antibody genes. In one embodiment, the parent antibody has been affinity matured, as is known in the art. Alternatively, the antibody has been modified in some other way, for example as described in U.S. Ser. No. 10/339, 788, filed on Mar. 3, 2003.

In certain embodiments, the Fc proteins described herein is substantially encoded by immunoglobulin genes belonging to any of the antibody classes. In an exemplary embodiment, the Fc proteins described herein find use in antibodies or Fc fusions that comprise sequences belonging to the IgG class of antibodies, including IgG1, IgG2, IgG3, or IgG4. In an alternate embodiment the Fc proteins described herein find use in antibodies or Fc fusions that comprise sequences belonging to the IgA (including subclasses IgA1 and IgA2), IgD, IgE, IgG, or IgM classes of antibodies. In some embodiments, the Fc proteins described herein comprise more than one protein chain. That is, in some embodiments, the polypeptides described herein find use in an antibody or Fc fusion that is a monomer or an oligomer, including a homo- or hetero-oligomer.

In some embodiments, the antibodies of the invention are based on human sequences, and thus human sequences are used as the "base" sequences, against which other sequences, such as rat, mouse, and monkey sequences are compared. In order to establish homology to primary sequence or structure, the amino acid sequence of a precursor or parent Fc polypeptide is directly compared to the human Fc sequence outlined herein. After aligning the sequences, using one or more of the homology alignment programs known in the art (for example using conserved residues as between species), allowing for necessary insertions and deletions in order to maintain alignment (i.e., avoiding the elimination of conserved residues through arbitrary deletion and insertion), the residues equivalent to particular amino acids in the primary sequence of human Fc are defined. Alignment of conserved residues preferably should conserve 100% of such residues. However, alignment of greater than 75% or as little as 50% of conserved residues is also adequate to define equivalent residues (sometimes referred to as "corresponding residues"). Equivalent residues may also be defined by determining homology at the level of tertiary structure for an Fc polypeptide whose tertiary structure has been determined. Equivalent residues are defined as those for which the atomic coordinates of two or more of the main chain atoms of a particular amino acid residue of the parent or precursor (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the Fc polypeptide.

In some embodiments, the Fc polypeptides described herein are combined with other Fc modifications, including but not limited to modifications that alter effector function or interaction with one or more Fc ligands. In certain embodiments, these combinations provide additive, synergistic, or properties in antibodies or Fc fusions. In one embodiment, the Fc proteins described herein is combined with other known Fc proteins (Duncan et al., 1988, Nature 332:563-564; Lund et al., 1991, J Immunol 147:2657-2662; Lund et al., 1992, Mol Immunol 29:53-59; Alegre et al., 1994, Transplantation 57:1537-1543; Hutchins et al., 1995, Proc Natl Acad Sci USA 92:11980-11984; Jefferis et al., 1995, Immunol Left 44:111-117; Lund et al., 1995, Faseb J 9:115-119; Jefferis et al., 1996, Immunol Left 54:101-104; Lund et al., 1996, J Immunol 157:4963-4969; Armour et al., 1999, Eur J Immunol 29:2613-2624; Idusogie et al., 2000, J Immunol 164:4178-4184; Reddy et al., 2000, J Immunol 164:1925-1933; Xu et al., 2000, Cell Immunol 200:16-26; Idusogie et al., 2001, J Immunol 166:2571-2575; Shields et al., 2001, J Biol Chem 276:6591-6604; Jefferis et al., 2002, Immunol Lett 82:57-65; Presta et al., 2002, Biochem Soc Trans 30:487-490; Hinton et al., 2004, J Biol Chem 279:6213-6216) (U.S. Pat. No. 5,624,821; U.S. Pat. No. 5,885,573; U.S. Pat. No. 6,194,551; PCT WO 00/42072; PCT WO 99/58572; US 2004/0002587 A1). In an alternate embodiment, the Fc proteins described herein are incorporated into an antibody or Fc fusion that comprises one or more engineered glycoforms. By "engineered glycoform" as used herein is meant a carbohydrate composition that is covalently attached to an Fc polypeptide, wherein said carbohydrate composition differs chemically from that of a parent Fc polypeptide. Engineered glycoforms may be useful for a variety of purposes, including but not limited to enhancing or reducing effector function. Engineered glycoforms may be generated by a variety of methods known in the art (Umana et al., 1999, Nat Biotechnol 17:176-180; Davies et al., 2001, Biotechnol Bioeng 74:288-294; Shields et al., 2002, J Biol Chem 277:26733-26740; Shinkawa et al., 2003, J Biol Chem 278:3466-3473); (U.S. Pat. No. 6,602,684; U.S. Ser. No. 10/277,370; U.S. Ser. No. 10/113,929; PCT WO 00/61739A1; PCT WO 01/29246A1; PCT WO 02/31140A1; PCT WO 02/30954A1); (Potelligent® technology [Biowa, Inc., Princeton, N.J.]; GlycoMAb® glycosylation engineering technology [GLYCART biotechnology AG, Zurich, Switzerland]). Many of these techniques are based on controlling the level of fucosylated and/or bisecting oligosaccharides that are covalently attached to the Fc region, for example by expressing an Fc polypeptide in various organisms or cell lines, engineered or otherwise (for example Lec-13 CHO cells or rat hybridoma YB2/0 cells), by regulating enzymes involved in the glycosylation pathway (for example FUT8 [.alpha.1,6-fucosyltransferase] and/or .beta.1-4-N-acetylglucosaminyltransferase III [GnTIII]), or by modifying carbohydrate(s) after the Fc polypeptide has been expressed. Engineered glycoform typically refers to the different carbohydrate or oligosaccharide; thus an Fc polypeptide, for example an antibody or Fc fusion, may comprise an engineered glycoform. Alternatively, engineered glycoform may refer to the Fc polypeptide that comprises the different carbohydrate or oligosaccharide. Thus combinations of the Fc proteins described herein with other Fc modifications, as well as undiscovered Fc modifications, are contemplated with the goal of generating antibodies or Fc fusions with optimized properties.

In certain embodiments, the variant Fc proteins and polypeptides described herein find use in an antibody. By "antibody described herein" as used herein is meant an antibody that comprises an Fc protein described herein. The present invention may, in fact, find use in any protein that comprises Fc, and thus application of the Fc polypeptide and proteins described herein is not limited to antibodies. The Fc proteins described herein may find use in an Fc fusion. By "Fc fusion described herein" as used herein refers to an Fc fusion that comprises an Fc protein described herein. Fc fusions may comprise an Fc protein described herein operably linked to a cytokine, soluble receptor domain, adhesion molecule, ligand, enzyme, peptide, or other protein or protein domain, and include but are not limited to Fc fusions described in U.S. Pat. No. 5,843,725; U.S. Pat. No. 6,018,026; U.S. Pat. No. 6,291,212; U.S. Pat. No. 6,291,646; U.S. Pat. No. 6,300,099; U.S. Pat. No. 6,323,323; PCT WO 00/24782; and in (Chamow et al., 1996, Trends Biotechnol 14:52-60; Ashkenazi et al., 1997, Curr Opin Immunol 9:195-200).

Virtually any antigen may be targeted by the proteins and polypeptides described herein, including but not limited to the following list of proteins, subunits, domains, motifs, and epitopes belonging to the following list of proteins: CD2; CD3, CD3E, CD4, CD11, CD11a, CD14, CD16, CD18, CD19, CD20, CD22, CD23, CD25, CD28, CD29, CD30, CD32, CD33 (p67 protein), CD38, CD40, CD40L, CD52, CD54, CD56, CD80, CD147, GD3, IL-1, IL-1R, IL-2, IL-2R, IL-4, IL-5, IL-6, IL-6R, IL-8, IL-12, IL-15, IL-18, IL-23, interferon alpha, interferon beta, interferon gamma; TNF-alpha, TNFbeta2, TNFc, TNFalphabeta, TNF-RI, TNF-RII, FasL, CD27L, CD30L, 4-1BBL, TRAIL, RANKL, TWEAK, APRIL, BAFF, LIGHT, VEG1, OX40L, TRAIL Receptor-1, A1 Adenosine Receptor, Lymphotoxin Beta Receptor, TALI, BAFF-R, EPO; LFA-3, ICAM-1, ICAM-3, $E_p$CAM, integrin beta1, integrin beta2, integrin alpha4/beta7, integrin alpha2, integrin alpha3, integrin alpha4, integrin alpha5, integrin alpha6, integrin alphav, alphaVbeta3 integrin, FGFR-3, Keratinocyte Growth Factor, VLA-1, VLA-4, L-selectin, anti-Id, E-selectin, HLA, HLA-DR, CTLA-4, T cell receptor, B7-1, B7-2, VNRintegrin, TGFbeta1, TGFbeta2, eotaxin1, BLyS (B-lymphocyte Stimulator), complement C5, IgE, factor VII, CD64, CBL, NCA 90, EGFR (ErbB-1), Her2/neu (ErbB-2), Her3 (ErbB-3), Her4 (ErbB-4), Tissue Factor, VEGF, VEGFR, endothelin receptor, VLA-4, Hapten NP-cap or NIP-cap, T cell receptor alpha/beta, E-selectin, digoxin, placental alkaline phosphatase (PLAP) and testicular PLAP-like alkaline phosphatase, transferrin receptor, Carcinoembryonic antigen (CEA), CEACAM5, HMFG PEM, mucin MUC1, MUC18, Heparanase 1, human cardiac myosin, tumor-associated glycoprotein-72 (TAG-72), tumor-associated antigen CA 125, Prostate specific membrane antigen (PSMA), High molecular weight melanoma-associated antigen (HMW-MAA), carcinoma-associated antigen, Geoprotein IIb/IIIa (GPIIb/IIIa), tumor-associated antigen expressing Lewis Y related carbohydrate, human cytomegalovirus (HCMV) gH envelope glycoprotein, HIV gp120, HCMV, respiratory syncital virus RSV F, RSVF Fgp, VNRintegrin, IL-8, cytokeratin tumor-associated antigen, Hep B gp120, CMV, gpIIbIIIa, HIV IIIB gp120 V3 loop, respiratory syncytial virus (RSV) Fgp, Herpes simplex virus (HSV) gD glycoprotein, HSV gB glycoprotein, HCMV gB envelope glycoprotein, and *Clostridium perfringens* toxin.

One skilled in the art will appreciate that the aforementioned list of targets refers not only to specific proteins and biomolecules, but the biochemical pathway or pathways that comprise them. For example, reference to CTLA-4 as a target antigen implies that the ligands and receptors that make up the T cell co-stimulatory pathway, including CTLA-4, B7-1, B7-2, CD28, and any other undiscovered ligands or receptors that bind these proteins, are also targets. Thus target as used herein refers not only to a specific biomolecule, but the set of proteins that interact with said target and the members of the biochemical pathway to which said target belongs. One skilled in the art will further appreciate that any of the aforementioned target antigens, the ligands or receptors that bind them, or other members of their corresponding biochemical pathway, may be operably linked to the Fc proteins described herein in order to generate an Fc fusion. Thus for example, an Fc fusion that targets EGFR could be constructed by operably linking an Fc protein to EGF, TGF.alpha., or any other ligand, discovered or undiscovered, that binds EGFR. Accordingly, an Fc protein described herein could be operably linked to EGFR in order to generate an Fc fusion that binds EGF, TGF.alpha., or any other ligand, discovered or undiscovered, that binds EGFR. Thus virtually any polypeptide, whether a ligand, receptor, or some other protein or protein domain, including but not limited to the aforementioned targets and the proteins that compose their corresponding biochemical pathways, may be operably linked to the Fc proteins described herein to develop an Fc fusion.

A number of antibodies and Fc fusions that are approved for use, in clinical trials, or in development benefit from the Fc proteins described herein. Said antibodies and Fc fusions are herein referred to as "clinical products and candidates". Thus in a preferred embodiment, the Fc proteins described herein may find use in a range of clinical products and candidates. For example, a number of antibodies that target CD20 may benefit from the Fc proteins described herein. For example the Fc proteins described herein may find use in an antibody that is substantially similar to rituximab (Rituxan®, IDEC/Genentech/Roche) (see for example U.S. Pat. No. 5,736,137), a chimeric anti-CD20 antibody approved to treat Non-Hodgkin's lymphoma; HuMax-CD20, an anti-CD20 currently being developed by Genmab, an anti-CD20 antibody described in U.S. Pat. No. 5,500,362, AME-133 (Applied Molecular Evolution), hA20 (Immunomedics, Inc.), and HumaLYM (Intracel). A number of antibodies that target members of the family of epidermal growth factor receptors, including EGFR (ErbB-1), Her2/neu (ErbB-2), Her3 (ErbB-3), Her4 (ErbB-4), may benefit from the Fc proteins described herein. For example the Fc proteins described herein may find use in an antibody that is substantially similar to trastuzumab (Herceptin®, Genentech) (see for example U.S. Pat. No. 5,677,171), a humanized anti-Her2/neu antibody approved to treat breast cancer; pertuzumab (rhuMab-2C4, Omnitarg®), currently being developed by Genentech; an anti-Her2 antibody described in U.S. Pat. No. 4,753,894; cetuximab (Erbitux®), Imclone) (U.S. Pat. No. 4,943,533; PCT WO 96/40210), a chimeric anti-EGFR antibody in clinical trials for a variety of cancers; ABX-EGF (U.S. Pat. No. 6,235,883), currently being developed by Abgenix/Immunex/Amgen; HuMax-EGFr (U.S. Ser. No. 10/172,317), currently being developed by Genmab; 425, EMD55900, EMD62000, and EMD72000 (Merck KGaA) (U.S. Pat. No. 5,558,864; Murthy et al. 1987, Arch Biochem Biophys. 252(2):549-60; Rodeck et al., 1987, J Cell Biochem. 35(4):315-20; Kettleborough et al., 1991, Protein Eng. 4(7):773-83); ICR62 (Institute of Cancer Research) (PCT WO 95/20045; Modjtahedi et al., 1993, J. Cell Biophys. 1993, 22(1-3):129-46; Modjtahedi et al., 1993, Br J. Cancer. 1993, 67(2):247-53; Modjtahedi et al., 1996, Br J Cancer, 73(2):228-35; Modjtahedi et al., 2003, Int J Cancer, 105(2):273-80); TheraClM hR3 (YM Biosciences, Canada and Centro de Immunologia Molecular, Cuba (U.S. Pat. No. 5,891,996; U.S. Pat. No. 6,506,883; Mateo et al., 1997, Immunotechnology, 3(1):71-81); mAb-806 (Ludwig Institue for Cancer Research, Memorial Sloan-Kettering) (Jungbluth et al. 2003, Proc Natl Acad Sci USA. 100(2):639-44); KSB-102 (KS Biomedix); MR1-1 (IVAX, National Cancer Institute) (PCT WO 0162931A2); and SC100 (Scancell) (PCT WO 01/88138). In another preferred embodiment, the Fc proteins described herein may find use in alemtuzumab (Campath®, Millenium), a humanized monoclonal antibody currently approved for treatment of B-cell chronic lymphocytic leukemia. The Fc proteins described herein may find use in a variety of antibodies or Fc fusions that are substantially similar to other clinical products and candidates, including but not limited to muromonab-CD3 (Orthoclone OKT3®), an anti-CD3 antibody developed by Ortho Biotech/Johnson & Johnson, ibritumomab tiuxetan (Zevalin®), an anti-CD20 antibody developed by IDEC/Schering AG, gemtuzumab ozogamicin (Mylotarg®), an anti-CD33 (p67 protein) antibody developed by Celltech/Wyeth, alefacept (Amevive®), an anti-LFA-3 Fc fusion developed by Biogen), abciximab (ReoPro®), developed by Centocor/Lilly, basiliximab (Simulect®), developed by Novartis, palivizumab (Synagis®), developed by MedImmune, infliximab (Remicade®), an anti-TNFalpha antibody developed by Centocor, adalimumab (Humira®), an anti-TNFalpha antibody developed by Abbott, Humicade®, an anti-TNFalpha antibody developed by Celltech, etanercept (Enbrel®), an anti-TNFalpha Fc fusion developed by Immunex/Amgen, ABX-CBL, an anti-CD147 antibody being developed by Abgenix, ABX-IL8, an anti-IL8 antibody being developed by Abgenix, ABX-MA1, an anti-MUC18 antibody being developed by Abgenix, Pemtumomab (R1549, .sup.90Y-muHMFG 1), an anti-MUC1 In development by Antisoma, Therex (R1550), an anti-MUC1 antibody being developed by Antisoma, AngioMab (AS1405), being developed by Antisoma, HuBC-1, being developed by Antisoma, Thioplatin (AS1407) being developed by Antisoma, Antegren®) (natalizumab), an anti-alpha-4-beta-1 (VLA-4) and alpha-4-beta-7 antibody being developed by Biogen, VLA-1 mAb, an anti-VLA-1 integrin antibody being developed by Biogen, LTBR mAb, an anti-lymphotoxin beta receptor (LTBR) antibody being developed by Biogen, CAT-152, an anti-TGF.beta.2 antibody being developed by Cambridge Antibody Technology, J695, an anti-IL-12 antibody being developed by Cambridge Antibody Technology and Abbott, CAT-192, an anti-TGF.beta.1 antibody being developed by Cambridge Antibody Technology and Genzyme, CAT-213, an anti-Eotaxin1 antibody being developed by Cambridge Antibody Technology, LymphoStat-B® an anti-Blys antibody being developed by Cambridge Antibody Technology and Human Genome Sciences Inc., TRAIL-R1 mAb, an anti-TRAIL-R1 antibody being developed by Cambridge Antibody Technology and Human Genome Sciences, Inc., Avastin® (bevacizumab, rhuMAb-VEGF), an anti-VEGF antibody being developed by Genentech, an anti-HER receptor family antibody being developed by Genentech, Anti-Tissue Factor (ATF), an anti-Tissue Factor antibody being developed by Genentech, Xolair® (Omalizumab), an anti-IgE antibody being developed by Genentech, Raptiva® (Efalizumab), an anti-CD1a antibody being developed by Genentech and Xoma, MLN-02 Antibody (formerly LDP-02), being developed by Genentech and Millenium Pharmaceuticals, HuMax CD4, an anti-CD4 antibody being developed by Genmab, HuMax-IL15, an anti-IL15 antibody being developed by Genmab and Amgen, HuMax-Inflam, being developed by Genmab and Medarex, HuMax-Cancer, an anti-Heparanase 1 antibody being developed by Genmab and Medarex and Oxford GcoSciences, HuMax-Lymphoma, being developed by Genmab and Amgen, HuMax-TAC, being developed by Genmab, IDEC-131, and anti-CD40L antibody being developed by IDEC Pharmaceuticals, IDEC-151 (Clenoliximab), an anti-CD4 antibody being developed by IDEC Pharmaceuticals, IDEC-114, an anti-CD80 antibody being developed by IDEC Pharmaceuticals, IDEC-152, an anti-CD23 being developed by IDEC Pharmaceuticals, anti-macrophage migration factor (MIF) antibodies being developed by IDEC Pharmaceuticals, BEC2, an anti-idiotypic antibody being developed by Imclone, IMC-1C11, an anti-KDR antibody being developed by Imclone, DC101, an anti-flk-1 antibody being developed by Imclone, anti-VE cadherin antibodies being developed by Imclone, CEA-Cide® (labetuzumab), an anti-carcinoembryonic antigen (CEA) antibody being developed by Immunomedics, LymphoCide® (Epratuzumab), an anti-CD22 antibody being developed by Immunomedics, AFP-Cide, being developed by Immunomedics, MyelomaCide, being developed by Immunomedics, LkoCide, being developed by Immunomedics, ProstaCide, being developed by Immunomedics, MDX-010, an anti-CTLA4 antibody being developed by Medarex, MDX-060, an anti-CD30 antibody being developed by Medarex, MDX-070 being developed by Medarex, MDX-018 being developed by Medarex, Osidem® (IDM-1), and anti-Her2 antibody being developed by Medarex and Immuno-Designed Molecules, HuMax®-CD4, an anti-CD4 antibody being developed by Medarex and Genmab, HuMax-IL 15, an anti-IL15 antibody being developed by Medarex and Genmab, CNTO 148, an anti-TNF.alpha. antibody being developed by Medarex and Centocor/J&J, CNTO 1275, an anti-cytokine antibody being developed by Centocor/J&J, MOR101 and MOR102, anti-intercellular adhesion molecule-1 (ICAM-1) (CD54) antibodies being developed by MorphoSys, MOR201, an anti-fibroblast growth factor receptor 3 (FGFR-3) antibody being developed by MorphoSys, Nuvion® (visilizumab), an anti-CD3 antibody being developed by Protein Design Labs, HuZAF®, an anti-gamma interferon antibody being developed by Protein Design Labs, Anti-.quadrature.5.quadrature.1 Integrin, being developed by Protein Design Labs, anti-IL-12, being developed by Protein Design Labs, ING-1, an anti-Ep-CAM antibody being developed by Xoma, and MLN01, an anti-Beta2 integrin antibody being developed by Xoma.

Application of the Fc polypeptides, proteins to the aforementioned antibody and Fc fusion clinical products and candidates is not meant to be constrained to their precise composition. In some embodiments, the Fc proteins described herein are incorporated into the aforementioned clinical candidates and products, or into antibodies and Fc fusions that are substantially similar to them. In certain embodiments, the Fc proteins described herein are incorporated into versions of the aforementioned clinical candidates and products that are humanized, affinity matured, engineered, or modified in some other way. Furthermore, the entire polypeptide of the aforementioned clinical products and candidates need not be used to construct a new antibody or Fc fusion that incorporates the Fc proteins described herein; for example only the variable region of a clinical product or candidate antibody, a substantially similar variable region, or a humanized, affinity matured, engineered, or modified version of the variable region may be used. In another embodiment, the Fc proteins and polypeptides described herein are used in an antibody or Fc fusion that binds to the same epitope, antigen, ligand, or receptor as one of the aforementioned clinical products and candidates.

In an aspect the Fc polypeptides described herein are used in a wide range of antibody and Fc fusion products. In one embodiment the antibody or Fc fusion comprising the Fc polypeptide or protein described herein is a therapeutic, a diagnostic, or a research reagent, preferably a therapeutic. In certain other embodiments, the antibodies and Fc fusions comprise the Fc based polypeptides described herein and are used for agricultural or industrial uses. In an alternate embodiment, the Fc proteins and polypeptides described herein compose a library that is screened experimentally. In certain embodiments, this library comprises a list of nucleic acid or amino acid sequences. In certain other embodiments, the library is a physical composition of nucleic acids or polypeptides that encode the library sequences. In some embodiments, the Fc proteins find use in an antibody composition that is monoclonal or polyclonal. The antibodies and Fc fusions described herein encompass, but are not restricted to agonists, antagonists, neutralizing, inhibitory, or stimulatory. In an exemplary embodiment, the antibodies and Fc fusions described herein are used to kill target cells that bear the target antigen, for example cancer cells. In an alternate embodiment, the antibodies and Fc fusions described herein are used to block, antagonize, or agonize the target antigen, for example for antagonizing a cytokine or cytokine receptor. In an alternate embodiment, the antibodies and Fc fusions described herein are used to block, antagonize, or agonize the target antigen and kill the target cells that bear the target antigen.

In some embodiments, the polypeptides disclosed herein are useful in regulating the immune response, e.g., in inhibiting the immune response in connection with autoimmune diseases or inflammatory diseases. Such polypeptides have therapeutic utility in treating and/or preventing an autoimmune disorder. Examples of autoimmune disorders that may be treated by administering the polypeptides of the disclosed herein include, but are not limited to, alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Meniere's disease, mixed connective tissue disease, multiple sclerosis, type 1 or immune-mediated diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjogren's syndrome, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis. Examples of inflammatory disorders include, but are not limited to, asthma, encephilitis, inflammatory bowel disease, chronic obstructive pulmonary disease (COPD), allergic disorders, septic shock, pulmonary fibrosis, undifferentitated spondyloarthropathy, undifferentiated arthropathy, arthritis, inflammatory osteolysis, and chronic inflammation resulting from chronic viral or bacteria infections. Examples of inflammatory disorders which can be prevented, treated or managed in accordance with the methods of the invention include, but are not limited to, asthma, encephilitis, inflammatory bowel disease, chronic obstructive pulmonary disease (COPD), allergic disorders, septic shock, pulmonary fibrosis, undifferentitated spondyloarthropathy, undifferentiated arthropathy, arthritis, inflammatory osteolysis, and chronic inflammation resulting from chronic viral or bacteria infections.

The Fc polypeptides described herein are used for various therapeutic purposes. In some embodiments, the Fc polypeptides and proteins are administered to a patient to treat an antibody-related disorder. A "patient" for the purposes described herein includes both humans and other animals, preferably mammals and most preferably humans. Thus the antibodies and Fc fusions described herein have both human therapy and veterinary applications. In the preferred embodiment the patient is a mammal, and in the most preferred embodiment the patient is human. The term "treatment" in the present invention is meant to include therapeutic treatment, as well as prophylactic, or suppressive measures for a disease or disorder. Thus, for example, successful administration of an antibody or Fc fusion prior to onset of the disease results in treatment of the disease. As another example, successful administration of an optimized antibody or Fc fusion after clinical manifestation of the disease to combat the symptoms of the disease comprises treatment of the disease. "Treatment" also encompasses administration of an optimized antibody or Fc fusion protein after the appearance of the disease in order to eradicate the disease. Successful administration of an agent after onset and after clinical symptoms have developed, with possible abatement of clinical symptoms and perhaps amelioration of the disease, comprises treatment of the disease. Those "in need of treatment" include mammals already having the disease or disorder, as well as those prone to having the disease or disorder, including those in which the disease or disorder is to be prevented. By "antibody related disorder" or "antibody responsive disorder" or "condition" or "disease" herein are meant a disorder that may be ameliorated by the administration of a pharmaceutical composition comprising an antibody or Fc fusion described herein. Antibody related disorders include but are not limited to autoimmune diseases, immunological diseases, infectious diseases, inflammatory diseases, neurological diseases, and oncological and neoplastic diseases including cancer. By "cancer" and "cancerous" herein refer to or describe the physiological condition in mammals that is typically characterized by unregulated cell growth. Examples of cancer include but are not limited to carcinoma, lymphoma, blastoma, sarcoma (including liposarcoma), neuroendocrine tumors, mesothelioma, schwanoma, meningioma, adenocarcinoma, melanoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophageal cancer, tumors of the biliary tract, as well as head and neck cancer. Furthermore, the Fc proteins described herein may be used to treat conditions including but not limited to congestive heart failure (CHF), vasculitis, rosacea, acne, eczema, myocarditis and other conditions of the myocardium, systemic lupus erythematosus, diabetes, spondylopathies, synovial fibroblasts, and bone marrow stroma; bone loss; Paget's disease, osteoclastoma; multiple myeloma; breast cancer; disuse osteopenia; malnutrition, periodontal disease, Gaucher's disease, Langerhans' cell histiocytosis, spinal cord injury, acute septic arthritis, osteomalacia, Cushing's syndrome, monoostotic fibrous dysplasia, polyostotic fibrous dysplasia, periodontal reconstruction, and bone fractures; sarcoidosis; multiple myeloma; osteolytic bone cancers, breast cancer, lung cancer, kidney cancer and rectal cancer; bone metastasis, bone pain management, and humoral malignant hypercalcemia, ankylosing spondylitisa and other spondyloarthropathies; transplantation rejection, viral infections, hematologic neoplasisas and neoplastic-like conditions for example, Hodgkin's lymphoma; non-Hodgkin's lymphomas (Burkitt's lymphoma, small lymphocytic lymphoma/chronic lymphocytic leukemia, mycosis fungoides, mantle cell lymphoma, follicular lymphoma, diffuse large B-cell lymphoma, marginal zone lymphoma, hairy cell leukemia and lymphoplamacytic leukemia), tumors of lymphocyte precursor cells, including B-cell acute lymphoblastic leukemia/lymphoma, and T-cell acute lymphoblastic leukemia/lymphoma, thymoma, tumors of the mature T and NK cells, including peripheral T-cell leukemias, adult T-cell leukemia/T-cell lymphomas and large granular lymphocytic leukemia, Langerhans cell histocytosis, myeloid neoplasias such as acute myelogenous leukemias, including AML with maturation, AML without differentiation, acute promyelocytic leukemia, acute myelomonocytic leukemia, and acute monocytic leukemias, myelodysplastic syndromes, and chronic myeloproliferative disorders, including chronic myelogenous leukemia, tumors of the central nervous system, e.g., brain tumors (glioma, neuroblastoma, astrocytoma, medulloblastoma, ependymoma, and retinoblastoma), solid tumors (nasopharyngeal cancer, basal cell carcinoma, pancreatic cancer, cancer of the bile duct, Kaposi's sarcoma, testicular cancer, uterine, vaginal or cervical cancers, ovarian cancer, primary liver cancer or endometrial cancer, and tumors of the vascular system (angiosarcoma and hemangiopericytoma), osteoporosis, hepatitis, HIV, AIDS, spondylartthritis, rheumatoid arthritis, inflammatory bowel diseases (IBD), sepsis and septic shock, Crohn's Disease, psoriasis, schleraderma, graft versus host disease (GVHD), allogenic islet graft rejection, hematologic malignancies, such as multiple myeloma (MM), myelodysplastic syndrome (MDS) and acute myelogenous leukemia (AML), inflammation associated with tumors, peripheral nerve injury or demyelinating diseases.

In one embodiment, an antibody or polypeptide described herein is administered to a patient having a disease involving inappropriate expression of a protein. Within the scope described herein this is meant to include diseases and disorders characterized by aberrant proteins, due for example to alterations in the amount of a protein present, the presence of a mutant protein, or both. An overabundance may be due to any cause, including but not limited to overexpression at the molecular level, prolonged or accumulated appearance at the site of action, or increased activity of a protein relative to normal. Included within this definition are diseases and disorders characterized by a reduction of a protein. This reduction may be due to any cause, including but not limited to reduced expression at the molecular level, shortened or reduced appearance at the site of action, mutant forms of a protein, or decreased activity of a protein relative to normal. Such an overabundance or reduction of a protein can be measured relative to normal expression, appearance, or activity of a protein, and said measurement may play an important role in the development and/or clinical testing of the antibodies and Fc fusions described herein.

In one embodiment, an antibody or polypeptide described herein is the only therapeutically active agent administered to a patient. Alternatively, the antibody or Fc fusion described herein is administered in combination with one or more other therapeutic agents, including but not limited to cytotoxic agents, chemotherapeutic agents, cytokines, growth inhibitory agents, anti-hormonal agents, kinase inhibitors, anti-angiogenic agents, cardioprotectants, or other therapeutic agents. Such molecules are suitably present in combination in amounts that are effective for the purpose intended. The skilled medical practitioner can determine empirically the appropriate dose or doses of other therapeutic agents useful herein. The antibodies and polypeptides described herein may be administered concomitantly with one or more other therapeutic regimens. For example, an antibody or polypeptide described herein may be administered to the patient along with chemotherapy, radiation therapy, or both chemotherapy and radiation therapy. In one embodiment, the antibody or Fc fusion described herein may be administered in conjunction with one or more antibodies or polypeptides, which may or may not comprise an Fc protein described herein.

In one embodiment, the antibodies and polypeptides described herein are administered with a chemotherapeutic agent. By "chemotherapeutic agent" as used herein is meant a chemical compound useful in the treatment of cancer. Examples of chemotherapeutic agents include but are not limited to alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL®, Bristol-Myers Squibb Oncology, Princeton, N.J.) and docetaxel (TAXOTERE®, Rhne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; thymidylate synthase inhibitor (such as Tomudex); cox-2 inhibitors, such as celicoxib (CELEBREX®) or MK-0966 (VIOXX®); and pharmaceutically acceptable salts, acids or derivatives of any of the above. Also included in this definition are anti-hormonal agents that act to regulate or inhibit hormone action on tumors such as anti estrogens including for example tamoxifen, raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; and pharmaceutically acceptable salts, acids or derivatives of any of the above.

In certain embodiments, a chemotherapeutic or other cytotoxic agent is administered as a prodrug. By "prodrug" as used herein is meant a precursor or derivative form of a pharmaceutically active substance that is less cytotoxic to tumor cells compared to the parent drug and is capable of being enzymatically activated or converted into the more active parent form. See, for example Wilman, 1986, Biochemical Society Transactions, 615th Meeting Belfast, 14:375-382; and Stella et al., "Prodrugs: A Chemical Approach to Targeted Drug Delivery," Directed Drug Delivery, Borchardt et al., (ed.): 247-267, Humana Press, 1985. The prodrugs that may find use with the present invention include but are not limited to phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use with the antibodies and Fc fusions described herein include but are not limited to any of the aforementioned chemotherapeutic agents.

In some embodiments, the proteins and polypeptides described herein are combined with other therapeutic regimens. For example, in one embodiment, the patient to be treated with the antibody or Fc fusion also receives radiation therapy. Radiation therapy can be administered according to protocols commonly employed in the art and known to the skilled artisan. Such therapy includes but is not limited to cesium, iridium, iodine, or cobalt radiation. In some embodiments, the radiation therapy is whole body irradiation, or directed locally to a specific site or tissue in or on the body, such as the lung, bladder, or prostate. Typically, radiation therapy is administered in pulses over a period of time from about 1 to 2 weeks. In some embodiments, the radiation therapy is administered over longer periods of time. In one embodiment, radiation therapy is administered to patients having head and neck cancer for about 6 to about 7 weeks. Optionally, the radiation therapy is administered as a single dose or as multiple, sequential doses. The skilled medical practitioner can determine empirically the appropriate dose or doses of radiation therapy useful herein. In accordance with another embodiment of the invention, the antibody or Fc fusion described herein and one or more other anti-cancer therapies are employed to treat cancer cells ex vivo. It is contemplated that such ex vivo treatment may be useful in bone marrow transplantation and particularly, autologous bone marrow transplantation. In certain embodiments, treatment of cells or tissue(s) containing cancer cells with antibody or Fc fusion and one or more other anti-cancer therapies, such as described above, is employed to deplete or substantially deplete the cancer cells prior to transplantation in a recipient patient. II certain embodiments, the proteins and Fc fusions of the invention are employed in combination with still other therapeutic techniques such as surgery.

In an alternate embodiment, the antibodies and polypeptides described herein are administered with a cytokine. By "cytokine" as used herein is meant a generic term for proteins released by one cell population that act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

A variety of other therapeutic agents find use for administration with the Fc variant proteins and polypeptides described herein. In one embodiment, the protein is administered with an anti-angiogenic agent. By "anti-angiogenic agent" as used herein is meant a compound that blocks, or interferes to some degree, the development of blood vessels. The anti-angiogenic factor may, for instance, be a small molecule or a protein, for example an antibody, Fc fusion, or cytokine, that binds to a growth factor or growth factor receptor involved in promoting angiogenesis. The preferred anti-angiogenic factor herein is an antibody that binds to Vascular Endothelial Growth Factor (VEGF). In an alternate embodiment, the antibody or Fc fusion is administered with a therapeutic agent that induces or enhances adaptive immune response, for example an antibody that targets CTLA-4. In an alternate embodiment, the antibody or Fc fusion is administered with a tyrosine kinase inhibitor. By "tyrosine kinase inhibitor" as used herein is meant a molecule that inhibits to some extent tyrosine kinase activity of a tyrosine kinase. Examples of such inhibitors include but are not limited to quinazolines, such as PD 153035, 4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis(4-fluoroanilino) phthalimide); tyrphostines containing nitrothiophene moieties; PD-0183805 (Warner-Lambert); antisense molecules (e.g. those that bind to ErbB-encoding nucleic acid); quinoxalines (U.S. Pat. No. 5,804,396); tryphostins (U.S. Pat. No. 5,804,396); ZD6474 (Astra Zeneca); PTK-787 (Novartis/Schering A G); pan-ErbB inhibitors such as C1-1033 (Pfizer); Affinitac (ISIS 3521; Isis/Lilly); Imatinib mesylate (ST1571, Gleevec®); Novartis); PKI 166 (Novartis); GW2016 (Glaxo SmithKline); C1-1033 (Pfizer); EKB-569 (Wyeth); Semaxinib (Sugen); ZD6474 (AstraZeneca); PTK-787 (Novartis/Schering AG); INC-1-C11 (Imclone); or as described in any of the following patent publications: U.S. Pat. No. 5,804,396; PCT WO 99/09016 (American Cyanamid); PCT WO 98/43960 (American Cyanamid); PCT WO 97/38983 (Warner-Lambert); PCT WO 99/06378 (Warner-Lambert); PCT WO 99/06396 (Warner-Lambert); PCT WO 96/30347 (Pfizer, Inc); PCT WO 96/33978 (AstraZeneca); PCT WO96/3397 (AstraZeneca); PCT WO 96/33980 (AstraZeneca), gefitinib (IRESSA®, ZD1839, AstraZeneca), and OSI-774 (Tarceva®, OSI Pharmaceuticals/Genentech).

A variety of linkers find use in the present invention to generate polypeptides (see definition above) or antibody—or polypeptides—conjugates (see definition below). By "linker", "linker sequence", "spacer", "tethering sequence" or grammatical equivalents thereof, herein is meant a molecule or group of molecules (such as a monomer or polymer) that connects two molecules and often serves to place the two molecules in a preferred configuration. A number of strategies may be used to covalently link molecules together. These include, but are not limited to polypeptide linkages between N- and C-termini of proteins or protein domains, linkage via disulfide bonds, and linkage via chemical cross-linking reagents. In one aspect of this embodiment, the linker is a peptide bond, generated by recombinant techniques or peptide synthesis. Choosing a suitable linker for a specific case where two polypeptide chains are to be connected depends on various parameters, including but not limited to the nature of the two polypeptide chains (e.g., whether they naturally oligomerize), the distance between the N- and the C-termini to be connected if known, and/or the stability of the linker towards proteolysis and oxidation. Furthermore, the linker may contain amino acid residues that provide flexibility. Thus, the linker peptide may predominantly include the following amino acid residues: Gly, Ser, Ala, or Thr. The linker peptide should have a length that is adequate to link two molecules in such a way that they assume the correct conformation relative to one another so that they retain the desired activity. Suitable lengths for this purpose include at least one and not more than 30 amino acid residues. Preferably, the linker is from about 1 to 30 amino acids in length, with linkers of 1, 2, 3, 4, 5, 6, 7, 8, 9, 10, 11, 12, 13, 14, 15, 16, 17, 18 19 and 20 amino acids in length being preferred. In addition, the amino acid residues selected for inclusion in the linker peptide should exhibit properties that do not interfere significantly with the activity of the polypeptide. Thus, the linker peptide on the whole should not exhibit a charge that would be inconsistent with the activity of the polypeptide, or interfere with internal folding, or form bonds or other interactions with amino acid residues in one or more of the monomers that would seriously impede the binding of receptor monomer domains. Useful linkers include glycine-serine polymers (including, for example, (GS)n, (GSGGS)n, (GGGGS)n and (GGGS)n, where n is an integer of at least one), glycine-alanine polymers, alanine-serine polymers, and other flexible linkers such as the tether for the shaker potassium channel, and a large variety of other flexible linkers, as will be appreciated by those in the art. Glycine-serine polymers are preferred since both of these amino acids are relatively unstructured, and therefore may be able to serve as a neutral tether between components. Secondly, serine is hydrophilic and therefore able to solubilize what could be a globular glycine chain. Third, similar chains have been shown to be effective in joining subunits of recombinant proteins such as single chain antibodies. Suitable linkers may also be identified by screening databases of known three-dimensional structures for naturally occurring motifs that can bridge the gap between two polypeptide chains. In a preferred embodiment, the linker is not immunogenic when administered in a human patient. Thus linkers may be chosen such that they have low immunogenicity or are thought to have low immunogenicity. For example, a linker may be chosen that exists naturally in a human. In a preferred embodiment the linker has the sequence of the hinge region of an antibody, that is the sequence that links the antibody Fab and Fc regions; alternatively the linker has a sequence that comprises part of the hinge region, or a sequence that is substantially similar to the hinge region of an antibody. Another way of obtaining a suitable linker is by optimizing a simple linker, e.g., (Gly4Ser)n, through random mutagenesis. Alternatively, once a suitable polypeptide linker is defined, additional linker polypeptides can be created to select amino acids that more optimally interact with the domains being linked. Other types of linkers that may be used in the present invention include artificial polypeptide linkers and inteins. In another embodiment, disulfide bonds are designed to link the two molecules. In another embodiment, linkers are chemical cross-linking agents. For example, a variety of bifunctional protein coupling agents may be used, including but not limited to N-succinimidyl-3-(2-pyridyldithiol) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., 1971, Science 238:1098. Chemical linkers may enable chelation of an isotope. For example, Carbon-14-labeled 1-isothiocyanatobenzyl-3-methyldiethylene triaminepentaacetic acid (MX-DTPA) is an exemplary chelating agent for conjugation of radionucleotide to the antibody (see PCT WO 94/11026). The linker may be cleavable, facilitating release of the cytotoxic drug in the cell. For example, an acid-labile linker, peptidase-sensitive linker, dimethyl linker or disulfide-containing linker (Chari et al., 1992, Cancer Research 52: 127-131) may be used. Alternatively, a variety of nonproteinaceous polymers, including but not limited to polyethylene glycol (PEG), polypropylene glycol, polyoxyalkylenes, or copolymers of polyethylene glycol and polypropylene glycol, may find use as linkers, that is may find use to link the Fc variants described herein to a fusion partner to generate an Fc fusion, or to link the antibodies and polypeptides described herein to a conjugate.

In one embodiment, an antibody or polypeptide described herein is conjugated or operably linked to another therapeutic compound, referred to herein as a conjugate. The conjugate may be a cytotoxic agent, a chemotherapeutic agent, a cytokine, an anti-angiogenic agent, a tyrosine kinase inhibitor, a toxin, a radioisotope, or other therapeutically active agent. Chemotherapeutic agents, cytokines, anti-angiogenic agents, tyrosine kinase inhibitors, and other therapeutic agents have been described above, and all of these aforemention therapeutic agents may find use as antibody or Fc fusion conjugates. In an alternate embodiment, the antibody or Fc fusion is conjugated or operably linked to a toxin, including but not limited to small molecule toxins and enzymatically active toxins of bacterial, fungal, plant or animal origin, including fragments and/or variants thereof. Small molecule toxins include but are not limited to calicheamicin, maytansine (U.S. Pat. No. 5,208,020), trichothene, and CC1065. In one embodiment of the invention, the antibody or polypeptide is conjugated to one or more maytansine molecules (e.g. about 1 to about 10 maytansine molecules per antibody molecule). Maytansine may, for example, be converted to May-SS-Me which may be reduced to May-SH3 and reacted with modified antibody or Fc fusion (Chari et al., 1992, Cancer Research 52: 127-131) to generate a maytansinoid-antibody or maytansinoid-Fc fusion conjugate. Another conjugate of interest comprises an antibody or Fc fusion conjugated to one or more calicheamicin molecules. The calicheamicin family of antibiotics are capable of producing double-stranded DNA breaks at sub-picomolar concentrations. Dolastatin 10 analogs such as auristatin E (AE) and monomethylauristatin E (MMAE) may find use as conjugates for the Fc variants described herein (Doronina et al., 2003, Nat Biotechnol 21(7):778-84; Francisco et al., 2003 Blood 102(4):1458-65). Useful enzymatically active toxins include but are not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, PCT WO 93/21232. The present invention further contemplates a conjugate or fusion formed between an antibody or Fc fusion described herein and a compound with nucleolytic activity, for example a ribonuclease or DNA endonuclease such as a deoxyribonuclease (DNase).

In an alternate embodiment, an Fc variant protein described herein is conjugated or operably linked to a radioisotope to form a radioconjugate. A variety of radioactive isotopes are available for the production of radioconjugate antibodies and Fc fusions. Examples include, but are not limited to, $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu.

In yet another embodiment, an Fc varaint described herein is conjugated to a "receptor" (such streptavidin) for utilization in tumor pretargeting wherein the antibody-receptor or Fc fusion-receptor conjugate is administered to the patient, followed by removal of unbound conjugate from the circulation using a clearing agent and then administration of a "ligand" (e.g. avidin) which is conjugated to a cytotoxic agent (e.g. a radionucleotide). In an alternate embodiment, the antibody or Fc fusion is conjugated or operably linked to an enzyme in order to employ Antibody Dependent Enzyme Mediated Prodrug Therapy (ADEPT). ADEPT may be used by conjugating or operably linking the antibody or Fc fusion to a prodrug-activating enzyme that converts a prodrug (e.g. a peptidyl chemotherapeutic agent, see PCT WO 81/01145) to an active anti-cancer drug. See, for example, PCT WO 88/07378 and U.S. Pat. No. 4,975,278. The enzyme component of the immunoconjugate useful for ADEPT includes any enzyme capable of acting on a prodrug in such a way so as to covert it into its more active, cytotoxic form. Enzymes that are useful in the method of this invention include but are not limited to alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as .beta.-galactosidase and neuramimidase useful for converting glycosylated prodrugs into free drugs; beta-lactamase useful for converting drugs derivatized with .alpha.-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, for example, Massey, 1987, Nature 328: 457-458). Antibody-abzyme and Fc fusion-abzyme conjugates can be prepared for delivery of the abzyme to a tumor cell population.

Other modifications of the Fc Variants comprise linking said protein or poly-peptide to one of a variety of nonproteinaceous polymers, e.g., polyethylene glycol (PEG), polypropylene glycol, polyoxyalkylenes, or copolymers of polyethylene glycol and polypropylene glycol.

Pharmaceutical compositions are encompassed wherein a Fc variant protein or polypeptide or Fc fusion described herein and one or more therapeutically active agents are formulated. Formulations of the antibodies and Fc fusions described herein are prepared for storage by mixing said antibody or Fc fusion having the desired degree of purity with optional pharmaceutically acceptable carriers, excipients or stabilizers (Remington's Pharmaceutical Sciences 16th edition, Osol, A. Ed., 1980), in the form of lyophilized formulations or aqueous solutions. Acceptable carriers, excipients, or stabilizers are nontoxic to recipients at the dosages and concentrations employed, and include buffers such as phosphate, citrate, acetate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; sweeteners and other flavoring agents; fillers such as microcrystalline cellulose, lactose, corn and other starches; binding agents; additives; coloring agents; salt-forming counter-ions such as sodium; metal complexes (e.g. Zn-protein complexes); and/or non-ionic surfactants such as TWEEN®, PLURONICS® or polyethylene glycol (PEG). In a preferred embodiment, the pharmaceutical composition that comprises the antibody or Fc fusion described herein is in a water-soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine. The formulations to be used for in vivo administration are preferably sterile. This is readily accomplished by filtration through sterile filtration membranes or other methods.

In certain embodiments, the proteins and polypeptides disclosed herein are formulated as immunoliposomes. A liposome is a small vesicle comprising various types of lipids, phospholipids and/or surfactant that is useful for delivery of a therapeutic agent to a mammal. Liposomes containing the antibody or Fc fusion are prepared by methods known in the art, such as described in Epstein et al., 1985, Proc Natl Acad Sci USA, 82:3688; Hwang et al., 1980, Proc Natl Acad Sci USA, 77:4030; U.S. Pat. No. 4,485,045; U.S. Pat. No. 4,544,545; and PCT WO 97/38731. Liposomes with enhanced circulation time are disclosed in U.S. Pat. No. 5,013,556. The components of the liposome are commonly arranged in a bilayer formation, similar to the lipid arrangement of biological membranes. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. A chemotherapeutic agent or other therapeutically active agent is optionally contained within the liposome (Gabizon et al., 1989, J National Cancer Inst 81:1484).

In certain embodiments, the antibodies, polypeptides, and other therapeutically active agents are entrapped in microcapsules prepared by methods including but not limited to coacervation techniques, interfacial polymerization (for example using hydroxymethylcellulose or gelatin-microcapsules, or poly-(methylmethacylate) microcapsules), colloidal drug delivery systems (for example, liposomes, albumin microspheres, microemulsions, nano-particles and nanocapsules), and macroemulsions. Such techniques are disclosed in Remington's Pharmaceutical Sciences 16th edition, Osol, A. Ed., 1980. Sustained-release preparations may be prepared. Suitable examples of sustained-release preparations include semipermeable matrices of solid hydrophobic polymer, which matrices are in the form of shaped articles, e.g. films, or microcapsules. Examples of sustained-release matrices include polyesters, hydrogels (for example poly(2-hydroxyethyl-methacrylate), or poly(vinylalcohol)), polylactides (U.S. Pat. No. 3,773,919), copolymers of L-glutamic acid and gamma ethyl-L-glutamate, non-degradable ethylene-vinyl acetate, degradable lactic acid-glycolic acid copolymers such as the LUPRON DEPOTS (which are injectable microspheres composed of lactic acid-glycolic acid copolymer and leuprolide acetate), poly-D-(−)-3-hydroxybutyric acid, and ProLease®) (commercially available from Alkermes), which is a microsphere-based delivery system composed of the desired bioactive molecule incorporated into a matrix of poly-DL-lactide-co-glycolide (PLG).

In embodiments, the concentration of the therapeutically active antibody or polypeptide described herein in the formulation varies from about 0.1 to 100 weight %. In one embodiment, the concentration of the antibody or polypeptide is in the range of 0.003 to 1.0 molar. In order to treat a patient, a therapeutically effective dose of the antibody or polypeptide described herein may be administered. By "therapeutically effective dose" herein is meant a dose that produces the effects for which it is administered. The exact dose will depend on the purpose of the treatment, and will be ascertainable by one skilled in the art using known techniques. Dosages may range from 0.01 to 100 mg/kg of body weight or greater, for example 0.1, 1, 10, or 50 mg/kg of body weight, with 1 to 10 mg/kg being preferred. As is known in the art, adjustments for antibody or polypeptide degradation, systemic versus localized delivery, and rate of new protease synthesis, as well as the age, body weight, general health, gender, diet, time of administration, drug interaction and the severity of the condition may be necessary, and will be ascertainable with routine experimentation by those skilled in the art.

Administration of the pharmaceutical composition comprising a protein or polypeptide described herein in the form of a sterile aqueous solution, is done in a variety of ways, including, but not limited to orally, subcutaneously, intravenously, intranasally, intraotically, transdermally, topically (e.g., gels, salves, lotions, creams, etc.), intraperitoneally, intramuscularly, intrapulmonary (e.g., AERx® inhalable technology commercially available from Aradigm, or Inhance® pulmonary delivery system commercially available from Inhale Therapeutics), vaginally, parenterally, rectally, or intraocularly. In some instances, for example for the treatment of wounds, inflammation, etc., the antibody or Polypeptide may be directly applied as a solution or spray. As is known in the art, the pharmaceutical composition may be formulated accordingly depending upon the manner of introduction.

According to the teachings herein, a polypeptide can be prepared with a variant Fc region which has improved, or diminished, ADCC activity. Such molecules find applications in the treatment of different disorders.

In certain embodiments, the polypeptide variant with improved ADCC activity is employed in the treatment of diseases or disorders where destruction or elimination of tissue or foreign micro-organisms is desired. For example, the polypeptide may be used to treat cancer; inflammatory disorders; infections (e.g. bacterial, viral, fungal or yeast infections); and other conditions (such as goiter) where removal of tissue is desired, etc.

Where the polypeptide variant has diminished ADCC activity, such variants are used to treat diseases or disorders where a Fc region-containing polypeptide with long half-life is desired, but the polypeptide preferably does not have undesirable effector function(s). For example, in an embodiment, the Fc region-containing polypeptide is an anti-tissue factor (TF) antibody; anti-IgE antibody; and anti-integrin antibody (e.g. an anti-a$\alpha$4$\beta$7 antibody). The desired mechanism of action of such Fc region-containing polypeptides may be to block ligand-receptor binding pairs. Moreover, the Fc-region containing polypeptide with diminished ADCC activity may be an agonist antibody.

In an aspect are provided methods for generating Fc proteins that are subsequently screened experimentally to single out optimized Fc proteins. General methods for antibody molecular biology, expression, purification, and screening are described in Antibodies: A Laboratory Manual by Harlow & Lane, New York: Cold Spring Harbor Laboratory Press, 1988.

One embodiment described herein relates to a rational design process to identify Fc proteins with improved selectivity and binding affinity to the Fc receptors. In one aspect, the invention includes understanding the structural features associated with dynamic properties which drive the interaction between the Fc and its receptors. Another embodiment described herein provides a method for identifying Fc protein polypeptides based on their binding affinities to FcγRIIa, FcγRIIb, and FcγRIIIa, electrostatics, solvation, packing, packing density, hydrogen binding networks and entropic effects associated with the dynamic nature of the protein molecule. The method of the current invention further provides for constructing the in silico identified mutants by, for example site-directed mutagenesis and/or de novo synthesis, and expression in mammalian cells for in vitro validation.

In one embodiment described herein, the Fc protein polypeptides identified in silico are reverse engineered to create nucleic acids that encode the member sequences, that may then be cloned into host cells, expressed and assayed, if desired. These practices are carried out using well-known procedures. For example, a variety of methods that may find use in the present invention are described in Molecular Cloning—A Laboratory Manual, 3rd Ed. (Maniatis, Cold Spring Harbor Laboratory Press, New York, 2001).

Fc proteins are screened using a variety of methods, including but not limited to those that use in vitro assays, in vivo and cell-based assays, and selection technologies. Automation and high-throughput screening technologies may be utilized in the screening procedures. Screening may employ the use of a fusion partner or label.

Design Strategies

A rational design process was undertaken to design Fc proteins with multiple amino acid substitutions that synergistically provide enhanced selectivity and binding affinity to a target Fc receptor. Central to this process is the understanding of structural features and associated dynamic properties which drive the interaction between the Fc and its receptors. Starting with the known co-complex structure between the Fc and the FcγRIIIb, homology models were constructed for the receptors of question: FcγRIIa, FcγRIIb, and FcγRIIIa. Applying a proprietary suite of in silico structure and dynamics-based technologies (including but not limited to ZymeCAD™ and ResidueNetworks™ (as described in WO 2009/098596, US20070276791 and US 20080147360)), unique insights into the structure-function relationships of these protein-protein interactions were identified and led to the proposal of unique combinations of mutations which were predicted to preferentially bind to various Fc receptors, and in certain examples, with improved binding strength. The primary quantitative metric to evaluate the Fc proteins is the binding energies. However, a number of other parameters such as changes in electrostatics, solvation, packing and packing density, hydrogen binding networks and entropic effects associated with the dynamic nature of the protein molecule are also employed in selecting attractive Fc proteins.

WO 2009/098596 provides methods and systems of determining biopolymer profiles and correlations between structural units (residues) of a biopolymer based on sampling of the conformational space available to the molecule. The correlations between these structural units are further used to find coupled residue networks in the protein.

In one embodiment, the functional and/or biophysical properties of Fc proteins are screened in an in vitro assay. Assays may employ a variety of detection methods including but not limited to chromogenic, fluorescent, luminescent, or isotopic labels. Assay to detect ADCC include but are not limited to, ADCC reporter assays, cytotoxicity assays, chromium release assay, europium release assay, sulfur release assay, and flow cytometry. Examples of well known assays can be found in the art, for example in Stavenhagen et al. (2007) "Fc Optimization of Therapeutic Antibodies Enhances Their Ability to Kill Tumor Cells In vitro and Controls Tumor Expansion In vivo via low-affinity Activating Fcγ Receptors," Cancer Res. 67:882 and Stavenhagen et al. (2008) "Enhancing the potency of therapeutic monoclonal antibodies via Fc optimization," Adv. Enzyme Regul. 48:152.

The biological properties of the antibodies and polypeptides that comprise the Fc proteins described herein may be characterized in cell, tissue, and whole organism experiments. Drugs are often tested in animals, including but not limited to mice, rats, rabbits, dogs, cats, pigs, and monkeys, in order to measure a drug's efficacy for treatment against a disease or disease model, or to measure a drug's pharmacokinetics, toxicity, and other properties. Therapeutics are often tested in mice, including but not limited to nude mice, SCID mice, xenograft mice, and transgenic mice (including knock-ins and knockouts).

The invention will be more fully understood by reference to the following examples. They should not, however, be construed as limiting the scope of this invention. All literature and patent citations mentioned herein are expressly incorporated by reference.

Example 1

Illustration of Rational Design of Polypeptides Having a Combination of Mutations Selected for Producing Selected FcγR Binding Profile Antibodies Targeting the HER2/Neu Receptor:

The Human Epidermal growth factor Receptors (HERs) are proteins embedded in the cell membrane and communicate molecular signals from outside the cell to inside the cell, and turn genes on and off. The HER proteins regulate cell growth, survival, adhesion, migration, and differentiation—functions that are amplified or weakened in cancer cells. Human Epidermal growth factor Receptor 2"—a member of the epidermal growth factor receptor family, is a protein giving higher aggressiveness in breast cancers. HER2/neu has also been designated as CD340. Approximately 15-20 percent of breast cancers have an amplification of the HER2/neu gene or overexpression of its protein product. Overexpression of this receptor in breast cancer is associated with increased disease recurrence and worse prognosis. Because of its prognostic role as well as its ability to predict response to trastuzumab, breast tumors are routinely checked for overexpression of HER2/neu. Overexpression also occurs in other cancer such as ovarian cancer, stomach cancer, and biologically aggressive forms of uterine cancer, such as uterine serous endometrial carcinoma.

Trastuzumab is a humanized monoclonal antibody that binds to the domain IV of the extracellular segment of the HER2/neu receptor. Cells treated with trastuzumab undergo arrest during the G1 phase of the cell cycle so there is reduced proliferation. It has been suggested that trastuzumab induces some of its effect by downregulation of HER2/neu leading to disruption of receptor dimerization and signaling through the downstream PI3K cascade. P27Kip1 is then not phosphorylated and is able to enter the nucleus and inhibit cdk2 activity, causing cell cycle arrest. Also, trastuzumab suppresses angiogenesis by both induction of antiangiogenic factors and repression of proangiogenic factors. It is thought that a contribution to the unregulated growth observed in cancer could be due to proteolytic cleavage of HER2/neu that results in the release of the extracellular domain. Trastuzumab has been shown to inhibit HER2/neu ectodomain cleavage in breast cancer cells.

Design of a Polypeptide Comprising a Combination of Modifications that Produce a Selected FcγR Binding Profile:

Some of the proteins and polypeptides disclosed herein are designed based on the impact of selected amino acid substitutions to the protein interactions and dynamics, which are indicative of enthalpic and entropic changes, respectively. Relative changes to protein binding characteristics, especially compared to the wild-type system, can be optimized.

In this example, a polypeptide is designed with the goal of selecting amino acid mutations that increase binding selectivity to the FcγRIIIa receptor when compared to a wild-type antibody (Trastuzumab/Herceptin®). The rational design performed resulted in a quadruple variant (S239E/S298A/K326A/A327H). In the following example, the main strategies of introducing FcγRIIIa-specific electrostatic interactions and adding steric repulsion to both FcγRIIa and FcγRIIb receptors are highlighted such that the selectivity design goal was achieved. In some cases, the mutations' contribution to binding on one chain of the Fc is different than the other chain and these chain-specific effects are also demonstrated. The specific effects to binding as a result of each of the four mutations are discussed with the binding profile of the Fc variant being an overall synergistic combination of the structural and dynamic changes.

A327H as a Steric Selectivity Driver:

His327 is a much bulkier group compared to the wild-type alanine and this substitution is a main selectivity driver that has minimal impact on the FcγRIIIa receptor while being detrimental for FcγRIIa and FcγRIIb. As shown in FIG. 1, the binding interface and the protein-protein interactions with the FcγRIIIa are preserved with the addition of His327 when compared to the wild-type Fc, which suggests that binding will not be affected between these two partners. The primary factor for the interface stabilization is due to the presence of the sidechain hydroxyl group from Tyr132 in FcγRIIIa. This non-conserved moiety is not present in FcγRIIa and hence the addition of His327 resulted in a major destabilization of the binding interface, most notably with the rapid dynamics observed for the receptor's neighboring His134 residue (FIG. 1). It is anticipated that binding to the IIa receptor will be severely disrupted.

While FcγRIIIa and FcγRIIa share a conserved His134 residue that is differentially affected with the addition of His327 to the Fc, FcγRIIb contains of an even bulkier Arg134. While this residue is also perturbed with the His134 mutation, it is however able to adopt a pseudo-favorable conformation that is stabilized with a serine sidechain on the Fc (FIG. 1). It is expected that binding of the Fc to the III) receptor will be reduced but not abolished because of the stabilized Arg rotomer.

S239E as an Electrostatic General Stabilizer and a Selectivity Driver:

The mutation S239E displays Fc chain-specific interactions to the receptors thereby facilitating both of its roles as a general stabilizing mutation as well as a selectivity driver for the FcγRIIIa receptor.Glu239 on chain-B of the Fc (FIG. 1) is a general stabilizing residue across all three receptors as it is able to form a hydrogen bond with conserved Lys120 residues. General stabilizing residues are beneficial in protein variant design as they ensure that the integrity of the binding interfaces is maintained when numerous mutations are introduced within confined areas.

Figure 2:
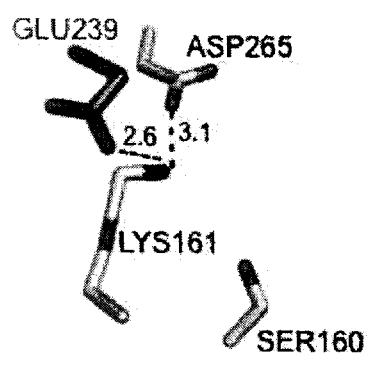
FIG. 2: Effects of the S239E mutation: A portion of the binding interface is shown between the chain-A of the antibody Fc (green) and the receptors (wheat) FcγRIIIa (left) and FcgRIIa & IIb (right). Mutated side-chain positions are colored in dark green with the residue labels in red. Dashed lines denote electrostatic interactions with the distances shown in angstroms (Å). FcγRIIa and FcγRIIb both contain conserved Tyr160 and Thr161 residues and are shown together for clarity.
Figure 2:
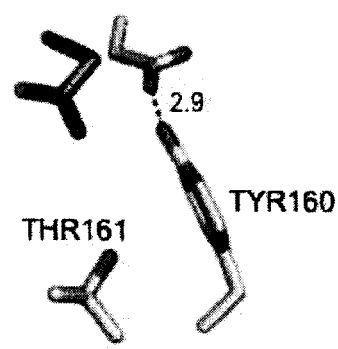

The S239E mutation, when introduced on chain-A of the Fc (FIG. 2) is a selectivity driver for improved FcγRIIIa binding as it is able to form a bifurcated electrostatic interaction with the non-conserved Lys161 while the enhanced binding interaction is not possible with the Thr161 in the FcγRIIa and IIb receptors.

S298A as Both a Steric and Electrostatic Selectivity Driver

Figure 3:
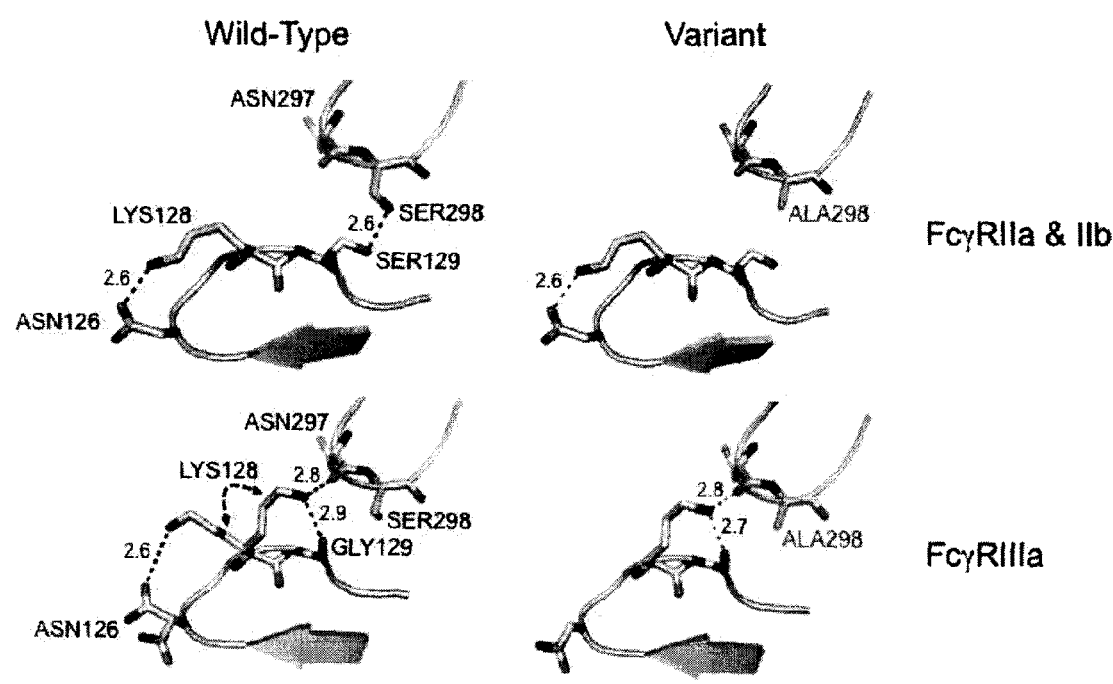
FIG. 3: Effects of the S298A mutation: A portion of the binding interface is shown between the chain-B of the antibody Fc (green) and the various Fcγ receptors (wheat). The wild-type Fc is shown on the left with the variant Fc shown on the right. Interactions with the FcγRIIa and IIb receptors are shown on the top while the FcγRIIIa is shown on the bottom. The S298A mutation is labeled in red with the dashed lines denoting electrostatic interactions with the intermolecular distances shown in angstroms (Å). For the FcγRIIIa system, the displayed conformations for Lys128 and Asn126 are the maximum allowable conformational movements with the intermediate conformers omitted for clarity.

The Ser298 residue in the wild-type antibody Fc interacts with Ser129 in the FcγRIIa and IIb receptors via hydrogen bonding while the receptors' Lys128 is stabilized intramolecularly and is not involved in any binding interactions (FIG. 3). The S298A mutation removes one of the key electrostatic binding partners between the Fc and the receptors and is therefore expected to drastically reduce binding to FcγRIIa and IIb receptors.

The wild-type Fc binds to the FcγRIIIa receptor using a different mechanism, with the interaction mediated by the backbone carbonyl group of Ser298 on the Fc with Lys128 from the receptor, which is able to partially occupy the binding interface. The sidechain flexibility and motions required for this interaction was demonstrated using molecular dynamics simulations (FIG. 3). The FcγRIIIa's Lys128 is 'locked' and pre-positioned in the binding conformation when the S298A mutation is introduced in the Fc.

Synergistic Combination of Mutations

By combining the above computational and structural insights in the Fc design process; the present disclosure provides a new variant that has, relative to the wild-type Fc, improved FcγRIIIa binding while having reduced binding to FcγRIIb and substantially abolished binding to FcγRIIa. As illustrated by in vitro binding assays with the resulting binding profile shown in FIG. 4.

Figure 4:
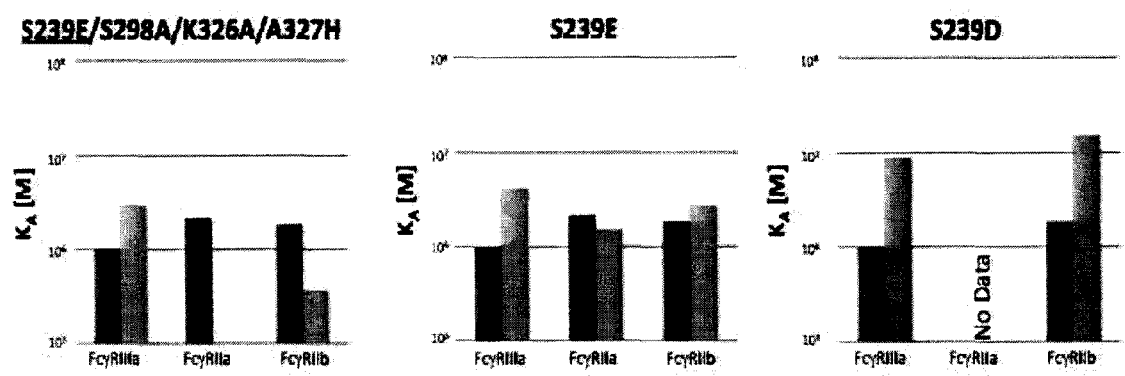
FIG. 4: In vitro binding profiles to the three Fcγ receptors: The in vitro binding (green) of the S239E/S298A/K326A/A327H variant (left) and the S239E control (right) were measured using surface plasmon resonance with binding reported as the association constant ($K_A$) in molar [M] in comparison to the wild-type Herceptin antibody (blue).

These results also demonstrate the unexpected synergistic nature of these mutations (FIG. 4). With the single S239E mutation, it is shown that the variants cannot clearly differentiate binding between the highly homologous receptors. With the addition of the S298A/K326A/A327H mutation combination, FcγRIIIa selectivity was improved.

Example 2

In Vitro and Ex Vivo Validation of Designed Antibodies

Once designed in silico individual antibodies are tested according to the methods described in Stavenhagen et al. (2007) *Cancer Res.* 67:882 and Stavenhagen et al. (2008), *Adv. Enzyme Regal.*, 48:152.

Briefly, the gene for each mutant is constructed by standard chemical synthesis using, for example, Trastuzumab IgG1 as the wild-type framework. After cloning into a suitable vector, the mutant Fc polypeptides are expressed in mammalian HEK293 cells. The FcγRIIa, FcγRIIb and FcγRIIIa are also cloned and expressed in HEK293 cells. The binding affinities of the antibodies to each of the three receptors is then determined by surface plasmon resonance.

Surface Plasmon Resonance Analysis:

Affinity of Fcγ receptors to antibody Fc was measure by SPR (surface Plasmon resonance) using a ProteOn XPR36 system from BIO-RAD. HER-2 in buffer (10 mM Hepes pH 6.8) was immobilized on CM5 chip through amine coupling until 3000 RU. Fc variants in an antibody format containing anti HER2 F(ab)$_2$ were immobilized to the HER-2 surface to 300 RU. Running buffer and the surfactant was maintained at pH 6.8. Purified analyte FcR was diluted in its running buffer and injected at a flow rate of 20-30 mul/min for 2 minutes, followed by dissociation for another 4 minutes. Five twofold dilutions of each antibody beginning at 20 nM were analyzed in triplicate. Sensograms were fit globally to a 1:1 Langmuir binding model. All experiments were conducted at room temperature. The in vitro binding Kd determined by SPR for each variant is shown in Table 1.

Antibody-Dependent Cellular Cytotoxicity Analysis:

The SKBR-3 cells were used as target cells in these experiments. A fresh vial of cryopreserved SKBR3 cells was thawed and a robust culture established. The SKBR3 cells were maintained in McKoy's medium enriched with 10% Fetal Bovine Serum and 1% PenStrep. The cells were passaged regularly upon attaining ~75% confluence (approximately every 3-4 days). To verify the binding of the variant antibodies to the target cells (SKBR3), binding curves for all variants and positive control (Herceptin) were obtained. SKBR-3 cells were washed with PBS and resuspended in FACS (Fluorescence-activated cell sorting) tubes at $2\times10^5$ cells per tube in 100 µl volume of PBS/1% BSA. Antibodies were added to the tubes to achieve 0.1, 1 and 10 µg/ml final concentration, cells incubated on ice for 1 hour, washed with 1% BSA/PBS and resuspended in 1:200 dilution of FITC-conjugated anti-human IgG. Cells were incubated on ice for another 40 min, washed again and resuspended in 200 µl of PBS. 10 µl of 10 mg/ml Propidium Iodide were added to each tube, and samples were analyzed by FACS. FACS gates were set to exclude dead cells (PI+). The Mean Fluorescence Intensity ("MFI") for each sample was measured. Cells stained with secondary but not primary antibody were used as negative control. As measured from the fold-difference in mean fluorescence intensity ("MFI"), all variants demonstrated levels of binding comparable to Herceptin.

To establish an effector:target cell (E:T) ratio and duration of incubation to achieve suitable cell killing, a preliminary ADCC experiment was performed using Herceptin as a positive control. SKBR-3 cells were seeded in flat bottom 96 well plates a day prior to experiment, at $2\times10^4$ cells per well in 200 µl of culture media. PBMCs were purified from fresh buffy coats from five different donors using Ficoll gradient centrifugation, washed 3 times with PBS and resuspended in RPMI containing 10% Heat Inactivated FBS and 10 ng/ml IL-2. Twenty four hours later, three wells containing SKBR-3 cells were trypsinized to verify cell count and to determine the exact number of PBMCs required to achieve the desired E:T ratio. Target cells were labeled with 10 µg/ml CFSE immediately prior of assay. Antibody (Herceptin) was added to cells at 1 and 10 µg/ml and incubated for 15 min. PBMCs at 10:1, 50:1 and 100:1 effector:target (E:T) ratio were then added to corresponding wells, and plates were briefly spun down at low RPM to concentrate cells in the bottom of the wells. The plates were then incubated in a standard tissue culture incubator for four, eight and twenty four hours. Following treatment, cells were harvested and added to 400 µl PBS containing propidium iodide ("PI"), a viability stain, and immediately analyzed by FACS. The extent of ADCC activity was determined by measuring the frequency of $PI^+$ green cells (killed targets) as the fraction of total target cells ($PI^-$ and $PI^+$ green cells). The pilot ADCC experiment demonstrated significant ADCC activity of Herceptin in SKBR3 cells. At 24 hours, higher E:T ratios (50:1 and 100:1) appeared to result in some antibody independent cell death. Because the killing of the cells at antibody concentrations of 1 and 10 µg/ml is indistinguishable, ADCC activity appears to be saturating above 1 µg/ml. Optimal results were observed at 24 hours with an E:T ratio of 10:1.

For the subsequent ADCC experiment, PBMCs from five buffy coats were purified using Ficoll gradient centrifugation. Following centrifugation and washes, cells were resuspended in 100 ml of pre-warmed RPMI. The cells were counted, and viability was determined by the Trypan Blue exclusion. An aliquot of cells from each donor was cryopreseved for future use. An additional aliquot of cells was used for FACS-based genotyping for the 158V/F CD16 polymorphism using a two-antibody staining protocol that exploits the fact that the G38 anti-CD16 antibody binds with equal affinity to both V and F alleles and comparing that with staining using the MEM-154 anti-CD16 antibody that has a lower affinity for the V allele than for the F allele (S. Bottcher et al., 2005, Journal of Immunological Methods, Volume 306, Issues 1-2, pp 128-136). Based on the CD16 genotyping results, samples from three donors heterozygous in the F/V, high cell viability and no endogenous cell killing were selected. All data points were obtained in triplicate wells and the viability for each donor was normalized to the viability of SKBR-3 cells incubated with PBMCs of the same donor, but without test antibody. The average ADCC results for these samples are summarized in Table 1.

As seen from table 1, the ex vivo ADCC assay revealed that a designed variants had significantly lowered ADCC than the wild-type antibody. This shows that the variations described herein are useful in modulating ADCC.

TABLE 1

Results from SPR and ADCC assay for different designed antibodies.

| Mutations Compared to Wildtype Trastuzumab | | | | | in vitro Binding Kd [M] | | | in silico ΔΔG solv [kcal/mol] | | | ex vivo ADCC assay |
|---|---|---|---|---|---|---|---|---|---|---|---|
| | | | | | IIIa (F) variant | IIa (H) variant | IIb variant | IIIa (F) variant | IIa (H) variant | IIb variant | Relative EC50 [µg/mL] |
| Wildtype Trastuzumab | | | | | 1.00E-06 | 4.62E-07 | 5.41E-07 | +++ | +++ | +++ | 1.0 |
| G237F | S239E | A327H | — | — | 1.58E-06 | 8.19E-06 | 1.16E-06 | ++++ | +++ | ++ | 0.7 |
| G237F | A327L | A330I | — | — | NB | NB | 1.46E-06 | ++ | ++++ | ++++ | 0.0 |
| S239E | A327L | A330I | — | — | 1.47E-06 | NB | 6.15E-06 | +++++ | ++ | + | ND |
| L235A | S239E | D265E | A327H | — | NB | NB | NB | +++++ | +++++ | + | 0.0 |
| S239E | S267E | H268D | — | — | 1.75E-07 | 6.42E-07 | 1.61E-08 | +++++ | +++++ | +++++ | 2.1 |
| G237F | S239E | D270N | — | — | NB | NB | NB | ++ | + | + | 1.0 |
| G236E | G237F | S239E | — | — | ND | NB | 8.56E-07 | +++ | + | + | ND |
| S239E | D265S | H268D | I332E | — | ND | 4.44E-06 | 4.16E-06 | ++++ | + | + | ND |
| S239E | D265S | I332E | — | — | 2.46E-06 | NB | NB | ++++ | +++ | + | ND |
| G237F | S239E | D265E | — | — | NB | NB | 2.95E-06 | +++++ | +++++ | + | ND |
| G237F | S239E | H268D | — | — | 5.94E-07 | 7.40E-07 | 6.84E-08 | +++ | +++++ | +++++ | 0.7 |
| S239D | D265S | S298A | I332E | | 1.04E-06 | NB | 4.01E-06 | +++ | ++ | +++++ | ND |
| S239E | S298A | K326A | A327H | — | 3.33E-07 | NB | 2.71E-06 | +++++ | ++ | ++ | ND |
| G237F | S298A | A330L | I332E | — | 4.29E-07 | NB | 7.63E-06 | +++ | +++ | ++++ | 5.3 |

TABLE 1-continued

Results from SPR and ADCC assay for different designed antibodies.

| Mutations Compared to Wildtype Trastuzumab | | | | | in vitro Binding Kd [M] | | | in silico ΔΔG solv [kcal/mol] | | | ex vivo ADCC assay |
|---|---|---|---|---|---|---|---|---|---|---|---|
| | | | | | IIIa (F) variant | IIa (H) variant | IIb variant | IIIa (F) variant | IIa (H) variant | IIb variant | Relative EC50 [μg/mL] |
| G236E | D270N | A327V | I332E | — | NB | NB | NB | +++++ | + | + | ND |
| H268E | D270E | S267G | — | — | 1.27E−06 | 5.31E−07 | 5.83E−07 | +++++ | +++++ | +++++ | ND |
| H268D | K326A | A327H | — | — | 1.33E−06 | 1.10E−06 | 2.71E−07 | ++++ | ++++ | +++++ | ND |
| H268D | E269L | S298A | K326A | A327H | 2.43E−06 | NB | 6.17E−06 | + | ++ | +++++ | ND |
| D265E | S267D | A330S | — | — | NB | NB | 1.59E−06 | + | +++++ | ++++ | 0.0 |

+++++ <−5 kcal/mol; ++++ −5 to −2 kcal/mol; +++ Between −2 and 2 kcal/mol; ++ 2 to 5 kcal/mol; + >5 kcal/mol NB: no binding; ND: Not Determined. Relative EC50: >1 = Enhanced ADCC; <1 = Supressed ADCC; ND = Not Determined

Example 3

Additional antibodies comprising modifications based on the in silico methods described above are summarized in Table 2.

TABLE 1

| Mutations | | | | | in silico ΔΔG solv [kcal/mol] | | | | | |
|---|---|---|---|---|---|---|---|---|---|---|
| | | | | | IIIa (F) variant | IIIa (V) variant | IIa (H) variant | IIa (R) variant | IIb (F) variant | IIb (Y) variant |
| WT Herceptin — | — | — | — | — | +++ | +++ | +++ | +++ | +++ | +++ |
| D270L | Y300L | A330K | — | — | + | + | +++++ | ++++ | ++++ | +++ |
| G236A | S239D | D270L | I332E | — | +++++ | +++++ | ++++ | ++ | +++++ | +++++ |
| G237F | S267G | N325F | — | — | + | +++ | +++ | + | ++ | + |
| G237F | V266L | S267D | — | — | ++ | ++ | +++ | ++++ | +++++ | ++++ |
| L234F | S267G | N325L | — | — | ++ | + | + | + | +++ | +++ |
| L234F | S267E | N325L | — | — | +++ | + | + | + | +++++ | ++++ |

+++++ <−5 kcal/mol; ++++ −5 to −2 kcal/mol; +++ Between −2 and 2 kcal/mol; ++ 2 to 5 kcal/mol; + > 5 kcal/mol NB: no binding; ND: Not Determined

Example 4

Treatment of Non-Hodgkins Lymphoma Using Anti-CD20 Antibodies

An antibody comprising a combination of modifications as described herein is administered to a patient having low-grade or follicular NHL. The recommended dosage for patients with low-grade or follicular NHL is 375 mg/m 2 infused i.v. at weekly intervals for a total of four doses. In a majority of patients, this can be accomplished in an outpatient clinic over a 22-day period.

Just before administration, the antibody preparation is diluted with 5% dextrose in water or 0.9% sodium chloride injection to a final concentration of 1-4 mg/mL. A 1-mg/mL dilution is preferable to facilitate adjustments in the infusion and to avoid adverse effects potentially caused by inadvertently rapid administration. Prepared infusions are stable in polyvinyl chloride or polyethylene bags at 2-8° C. (36-46° F.) for 24 hours and at room temperature for an additional 12 hours. Unused portions of undiluted drug must be discarded because of the absence of a preservative.

Thirty to 60 minutes before each infusion, acetaminophen 650-1000 mg and diphenhydramine hydrochloride 50-100 mg can be administered to help prevent infusion-related effects. Infusion may be through either a central or peripheral i.v. catheter but should never be given by i.v. push or bolus injection, owing to the risk of potentially serious infusion-related adverse effects. Before beginning each infusion, the administering clinician must prime the i.v. tubing with drug-containing solution to guarantee that active drug rather than other solution is being infused from the beginning. The first infusion should be initiated at 50 mg/hr with the rate increased by 50 mg/hr every 30 minutes as tolerated until a maximum rate of 400 mg/hr is reached. Subsequent infusions may be started at 100 mg/hr, with 100-mg/hr increases every 30 minutes as tolerated until the maximum rate (400 mg/hr) is attained. In patients with a large tumor burden (white blood cell count, >25,000/mm 3), an initial infusion rate of 25 mg/hr should be considered.

Example 5

Treatment of Systemic Lupus Erythematosus in Serologically-Active Patients

All subjects receive anti-CD22 antibodies incorporating the Fc polypeptide modifications described herein monthly, with loading doses on days 8 and 15 of month one, until disease progression or subject discontinuation. The drug is prepared in a 10 mg/ml prepared in 17.5 vials. Administration is carried out by slow intravenous infusion using PBS as a vehicle/buffer for the infusion procedures. All patients were given 1200 mg antibody given in 2 doses every other week in 12 week treatment cycles. Assessments of the patients treated were accomplished through a combined response index analysis evaluating BILAG, SLEDAI, and a physician's global assessment and treatment failure status.

Example 6

Treatment of BLL Using Anti-CD22 Antibodies

The dosage used is 120-1000-mg/m2 by infusion with diffuse large B-cell lymphoma.

Sub-CutaneousAdministration of Antibodies comprising the amino acid modifications described herein The subcutaneous immunoglobulin is infused in the sub-cutaneous tissue on the abdomen twice or thrice a week, with a maximal speed of 2 mL/h. Every time 20 mL is infused, the needle is removed to a new place.

Example 7

Administration of Immunoglobulin to Control Chronic Disease Such as Type B Hepatitis Continuous monthly administration of anti-hepatitis B antibodies incorporating the Fc polypeptides described herein at 5000 IU a month as a treatment results in reduced serum levels of the patient's own anti-hepatitis B antibodies and decreased symptoms of liver disease.

Example 8

Treatment of Organ Rejection Using Anti-CD20 Antibodies

Treatment of organ transplant patients is done either weekly, biweekly, bi-monthly, or monthly, by infusion of anti-CD20 antibodies comprising the amino acid modifications provided herein from 100 to 1000 mg/m2, according the above protocol for infusion and pretreatment.

The polypeptides and methods disclosed herein are used, without limitation to develop antibodies and polypeptides based on synergistic improvements to the Fc region of the following antibodies: Bevacizumab (Avastin); Abciximab (ReoPro); Adalimumab (Humira); Alemtuzumab (Campath); Cetuximab (Erbitux); Efalizumab (Raptiva); Etanercept (Enbrel); Gemtuzumab oxogamicin (Mylotarg); Infliximab (Remicade); Natalizumab (Tysabri, aka Antegren); Omalizumab (Xolair); Palivizumab (Syangis); Rituximab (Rituxan); Trastuzumab (Herceptin); Golimumab (Simponi); Panitumumab (Vectibix); Canakinumab (ILARIS); Ustekinumab (Stelara); Denosumab (Prolia); Ofatumumab (Arzerra)

While specific embodiments of the present invention have been shown and described herein, it will be obvious to those skilled in the art that such embodiments are provided by way of example only. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A polypeptide comprising a variant Fc region, wherein said variant Fc region comprises amino acid modifications relative to a wild-type Fc region, said amino acid modifications comprising a mutation at position 239 and further comprises the mutation D265S, wherein the numbering of amino acid residues is according to the EU index as set forth in Kabat, and wherein the mutation at position 239 is S239D or S239E.

2. The polypeptide of claim 1, wherein said modification at position 239 is S239E wherein the polypeptide has higher selectivity in binding to the FcγRIIIa receptor compared to a polypeptide comprising the wild-type Fc region.

3. The polypeptide of claim 1, wherein said modifications further comprise the mutation S298A.

4. The polypeptide of claim 1 wherein the polypeptide comprises the amino acid modifications S239D/D265S/S298A/I332E S239E/D265S/H268D/I332E, or S239E/D265S/I332E.

5. The polypeptide of claim 1, wherein the variant Fc region is based on a human IgG Fc region.

6. The polypeptide of claim 5, wherein the human IgG Fc region is a human IgG1, IgG2, IgG3, or IgG4 Fc region.

7. The polypeptide of claim 1 wherein said polypeptide is an antibody.

8. The polypeptide of claim 7, wherein said antibody is a monoclonal antibody, a humanized antibody, or a human antibody.

9. A therapeutic antibody comprising the polypeptide of claim 1.

10. The therapeutic antibody of claim 9, wherein said therapeutic antibody is based on a parent antibody selected from the group consisting of abagovomab, adalimumab, alemtuzumab, aurograb, bapineuzumab, basiliximab, belimumab, bevacizumab, briakinumab, canakinumab, catumaxomab, certolizumab pegol, cetuximab, daclizumab, denosumab, efalizumab, galiximab, gemtuzumab ozogamicin, golimumab, ibritumomab tiuxetan, infliximab, ipilimumab, lumiliximab, mepolizumab, motavizumab, muromonab, mycograb, natalizumab, nimotuzumab, ocrelizumab, ofatumumab, omalizumab, palivizumab, panitumumab, pertuzumab, ranibizumab, reslizumab, rituximab, teplizumab, tocilizumab/atlizumab, tositumomab, trastuzumab, VB4-847, girentuximab, ustekinumab, zalutumumab, and any other antibodies.

11. The therapeutic antibody of claim 9, wherein said therapeutic antibody binds to a target antigen selected from the group consisting of a-chain (CD25) of IL-2R, Amyloid beta, BLyS (or BAFF), CD11a, CD20, CD22, CD23, CD3, CD4, CD52, CD80, CTLA-4, EGFR, EpCAM, F protein of RSV, G250, glycoprotein IIb/IIIa R, HER2, Hsp90, IgE antibody, IL-12/IL-23, IL-1b, IL-5, IL-6 receptor, Integrin alpha-4/beta-1, Mucin 16/CA-125, RANKL, TNF alpha, and VEGF-A.

12. A pharmaceutical composition comprising a therapeutically effective amount of the polypeptide of claim 1, and a pharmaceutically acceptable carrier.

13. The polypeptide of claim 1 wherein the variant Fc region further comprises one or more mutations selected from the group consisting of: L234Q, L234N, L235A, G236E, E236L, E236D, G237F, G237N, S267E, S267D, S267G, H268D, H268E, E269L, E269L, D270N, D270I, D270E, S298A, K326A, K326D, A327H, A327V, A327L, A327T, A330V, A330L, A330W, A330I, A330S, I332L, I332D, and I332E.

14. The polypeptide of claim 1 wherein the variant Fc region further comprises one or more mutations selected from the group consisting of: S298A, K326A, K326D, A327H, A327V, A327L, A327T, I332L, I332D, and I332E.

* * * * *